(12) United States Patent
Schwögler et al.

(10) Patent No.: US 7,375,108 B2
(45) Date of Patent: May 20, 2008

(54) 2-SUBSTITUTED PYRIMIDINES

(75) Inventors: Anja Schwögler, Mannheim (DE); Markus Gewehr, Kastellaun (DE); Bernd Müller, Frankenthal (DE); Thomas Grote, Wachenheim (DE); Wassilios Grammenos, Ludwigshafen (DE); Jordi Tormo i Blasco, Laudenbach (DE); Andreas Gypser, Mannheim (DE); Joachim Rheinheimer, Ludwigshafen (DE); Carsten Blettner, Mannheim (DE); Peter Schäfer, Ottersheim (DE); Frank Schieweck, Hessheim (DE); Oliver Wagner, Neustadt (DE); Reinhard Stierl, Freinsheim (DE); Ulrich Schöfl, Brühl (DE); Siegfried Strathmann, Limburgerhof (DE); Maria Scherer, Godramstein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/564,013

(22) PCT Filed: Jul. 15, 2004

(86) PCT No.: PCT/EP2004/007877

§ 371 (c)(1),
(2), (4) Date: Jan. 9, 2007

(87) PCT Pub. No.: WO2005/012261

PCT Pub. Date: Feb. 10, 2005

(65) Prior Publication Data
US 2007/0105873 A1    May 10, 2007

(30) Foreign Application Priority Data

Jul. 24, 2003 (DE) .................... 103 33 857
Dec. 9, 2003 (DE) .................... 103 57 714

(51) Int. Cl.
C07D 239/42 (2006.01)
A01N 43/54 (2006.01)

(52) U.S. Cl. ............................ 514/256; 544/329

(58) Field of Classification Search ............ 544/329; 514/256
See application file for complete search history.

(56) References Cited

U.S. PATENT DOCUMENTS
2004/0116429 A1    6/2004    Grote et al.

FOREIGN PATENT DOCUMENTS

| CA | 2 467 683 A1 | 5/2003 |
|---|---|---|
| WO | WO-01/96314 A1 | 12/2001 |
| WO | WO-02/074753 A | 9/2002 |
| WO | WO-03/043993 A | 5/2003 |

*Primary Examiner*—Deepak Rao
(74) *Attorney, Agent, or Firm*—Birch, Stewart, Kolasch & Birch, LLP

(57) ABSTRACT

The invention relates to 2-substituted pyrimidines of the formula I

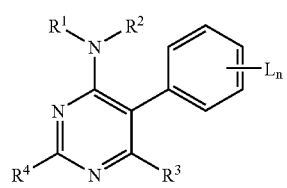

in which the index n and the substituents $R^1$ to $R^3$ and L are as defined in the description and
$R^4$ corresponds to one of the formulae

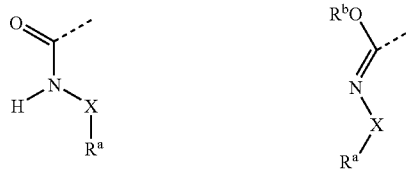

in which $R^a$, X and $R^b$ are as defined in the description; and also to processes for preparing these compounds, to pesticidal compositions comprising these compounds and to their use as pesticides.

14 Claims, No Drawings

2-SUBSTITUTED PYRIMIDINES

The invention relates to 2-substituted pyrimidines of the formula I

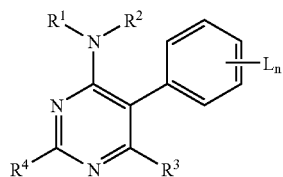

in which the index and the substituents are as defined below:

n is an integer from 1 to 5;

L is halogen, cyano, cyanato (OCN), $C_1$-$C_8$-alkyl, $C_2$-$C_8$-alkenyl, $C_2$-$C_8$-alkynyl, $C_1$-$C_6$-alkoxy, $C_2$-$C_8$-alkenyloxy, $C_2$-$C_8$-alkynyloxy, $C_3$-$C_6$-cycloalkyl, $C_4$-$C_6$-cycloalkenyl, $C_3$-$C_6$-cycoalkyloxy, $C_4$-$C_6$-cycloalkenyloxy, nitro, —C(=O)-A, —C(=O)—O-A, —C(=O)—N(A')A, C(A')(=N—OA), N(A')A, N(A')-C(=O)-A, N(A")-C(=O)—N(A')A, S(=O)$_m$-A, S(=O)$_m$—O-A or S(=O)$_m$—N(A')A, m is 0, 1 or 2;

A, A', A" independently of one another are hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, where the organic radicals may be partially or fully halogenated or may be substituted by nitro, cyanato, cyano or $C_1$-$C_4$-alkoxy; or A and A' together with the atoms to which they are attached are a five- or six-membered saturated, partially unsaturated or aromatic heterocycle which contains one to four heteroatoms from the group consisting of O, N and S;

where the aliphatic groups of the radical definitions of L for their part may be partially or fully halogenated or may carry one to four groups R";

R" is cyano, $C_1$-$C_6$-alkoxy, $C_3$-$C_6$-cycloalkyl, $C_2$-$C_8$-alkenyloxy, $C_2$-$C_8$-alkynyloxy, $C_4$-$C_6$-cycloalkenyl, $C_3$-$C_6$-cycloalkyloxy, $C_4$-$C_6$-cycloalkenyloxy, —C(=O)-A, —C(=O)—O-A, —C(=O)—N(A')A, C(A')(=N—OA), N(A')A, N(A')-C(=O)-A, N(A")-C(=O)—N(A')A, S(=O)$_m$-A, S(=O)$_m$—O-A or S(=O)$_m$—N(A')A;

$R^1$,$R^2$ independently of one another are $C_1$-$C_6$-alkyl, $C_2$-$C_6$-alkenyl, $C_2$-$C_6$-alkynyl, $C_3$-$C_6$-cycloalkyl, $C_3$-$C_6$-halocycloalkyl, where the aliphatic groups of the radical definitions of $R^1$ and $R^2$ for their part may be partially or fully halogenated or may carry one to four groups $R^v$:

$R^v$ is cyano, $C_3$-$C_6$-cycloalkyl, $C_4$-$C_6$-cycloalkenyl, hydroxyl, $C_1$-$C_6$-alkoxy, $C_2$-$C_8$-alkenyloxy, $C_2$-$C_8$-alkynyloxy, $C_3$-$C_6$-cycloalkyloxy, $C_4$-$C_6$-cycloalkenyloxy, $C_1$-$C_6$-alkylthio, —C(=O)-A, —C(=O)—O-A, —C(=O)—N(A')A, C(A')(=N—OA), N(A')A, N(A')-C(=O)-A, N(A")-C(=O)—N(A')A, S(=O)$_m$-A, S(=O)$_m$—O-A or S)=O)$_m$—N(A')A or phenyl, where the phenyl moiety may carry one to three radicals selected from the group consisting of: halogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_1$-$C_6$-alkoxy, cyano, nitro, —C(=O)-A, —C(=O)—O-A, —C(=O)—N(A')A, C(A')(=N—OA), N(A')A;

$R^2$ may additionally be hydrogen;

$R^1$ and $R^2$ may also, together with the nitrogen atom to which they are attached, form a saturated or unsaturated five- or six-membered ring which may be interrupted by an ether (—O—), carbonyl (C=O), thio (—S—), sulfoxyl (—S[=O]—) or sulfenyl (—SO$_2$—) or a further amino (—N($R^a$) group, where $R^a$ is hydrogen or $C_1$-$C_6$-alkyl, and/or may contain one or more substituents from the group consisting of halogen, $C_1$-$C_6$-alkyl, $C_1$-$C_6$-haloalkyl and oxy-$C_1$-$C_3$-alkyleneoxy;

$R^3$ is halogen, cyano, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy, $C_3$-$C_4$-alkenyloxy, $C_3$-$C_4$-alkynyloxy, $C_1$-$C_6$-alkylthio, di-($C_1$-$C_6$-alkyl)amino or $C_1$-$C_6$-alkylamino, where the alkyl, alkenyl and alkynyl radicals of $R^3$ may be substituted by halogen, cyano, nitro, $C_1$-$C_2$-alkoxy or $C_1$-$C_4$-alkoxycarbonyl;

$R^4$ corresponds to one of the formulae

where

X is a direct bond, —(C=O)—, —(C=O)—NH—, —(C=O)—O—, —O—, —$NR^c$—, —$CH_2$O—(C=O)—, —C=C—(C=O)—, where in each case the left atom of the bridge is attached to the nitrogen atom;

$R^a$ is hydrogen, $C_1$-$C_6$-alkyl, $C_2$-$C_8$-alkenyl, $C_2$-$C_8$-alkynyl or benzyl;

$R^b$ is hydrogen, $C_1$-$C_6$-alkyl, $C_2$-$C_6$-alkenyl or $C_2$-$C_6$-alkynyl;

$R^c$ is hydrogen, $C_1$-$C_6$-alkyl, $C_2$-$C_6$-alkenyl, $C_2$-$C_6$-alkynyl, benzyl or $C_1$-$C_6$-acyl, where the aliphatic, alicyclic or aromatic groups of the radical definitions of $R^a$, $R^b$ and/or $R^c$ for their part may carry one to four groups $R^w$:

$R^w$ is halogen, cyano, $OR^x$, $NHR^x$, $SR^x$, $C_1$-$C_6$-alkyl, $C_2$-$C_6$-alkenyl, $C_2$-$C_6$-alkynyl, $C_1$-$C_6$-alkoxy, $C_1$-$C_4$-alkoxycarbonyl, $C_1$-$C_4$-acylamino, [1,3]dioxolane-$C_1$-$C_4$-alkyl, [1,3]dioxane-$C_1$-$C_4$-alkyl, where $R^x$ is hydrogen, $C_1$-$C_6$-alkyl, $C_2$-$C_8$-alkenyl, $C_2$-$C_8$-alkynyl or benzyl.

Moreover, the invention relates to a process for preparing these compounds, to compositions comprising 2-pyrimidines and to their use for controlling phytopathogenic harmful fungi.

Fungicidal pyrimidines carrying a cyanamino substituent in the 2-position are known from WO-A 01/96314. Furthermore, fungicidal 2-pyrimidyl-N-methoxyamidines are known from WO-A 03/43993.

However, in many cases the activity of the abovementioned pyrimidines is unsatisfactory. It is an object of the present invention to provide compounds having improved activity.

We have found that this object is achieved by the pyrimidines of the formula I defined at the outset. Moreover, we have found processes for their preparation and compositions comprising them for controlling harmful fungi.

The compounds I can be obtained by different routes.

1) It is possible, for example, to use sulfones of the formula 11 whose preparation is described in detail in WO-A 02/074753 or DE 10156279.9 as starting materials. Reaction of the sulfones II with metal cyanides III (Me⁺CN⁻) yields the nitriles IV. Metal cyanides are to be understood as meaning primarily alkali metal cyanides or alkaline earth metal cyanides or else covalent cyanides, such as tin tetracyanide.

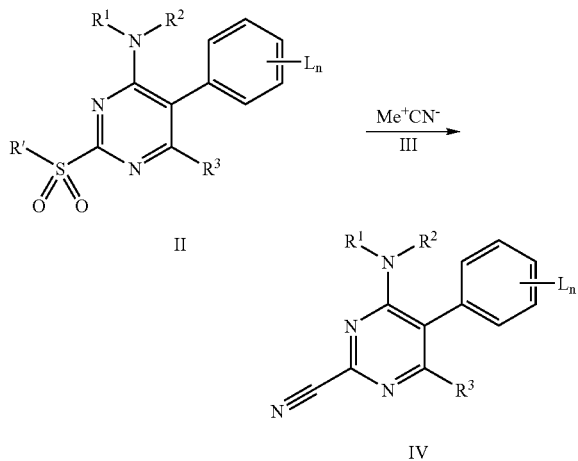

The exchange of the sulfonate group for the nitrile group is carried out by methods known from the literature, as described, for example, in WO-A 03/043993.

The further synthesis can be carried out as shown in Scheme 1:

The nitrile compound IV can be hydrolyzed to the amide IA under acidic or, preferably, basic conditions. The hydrolysis is carried out, for example, under the conditions described by Katritzky et al. in Synthesis 1989, pp. 949-950 (hydrogen peroxide, base, polar aprotic solvent). Hydrolyses of nitriles to amides under acidic conditions are described in Comprehensive Organic Chemistry, Vol 2, Sutherland, I.O. Pergamon Press, Oxford, 1979, p. 964.

Alternatively, the Pinner adduct, which is generated when in general hydrochloric acid forms an adduct with nitrile IV, can be reacted with an alcohol of the formula $R^bOH$, where $R^b$ is as defined above, to give the imino ether of the formula IB. The alkylation with $R^aX$—Y, where $R^a$ and the bridge X are as defined above and y is a leaving group such as halide, sulfate or sulfonate, gives compounds of type IC.

The alkylation with $R^a$—Y starting with compound IB or the nitrile IV can also be carried out using Meerwein salts of the formula $(R^a)_3OBF_4$ analogously to the procedures given in Synth. Commun., 1983, 13, p. 753 or Helv. Chim. Acta, 1986, 69, p. 1224. This affords compounds I in which X is a direct bond.

An alternative synthesis of the compounds IA according to the invention is shown in Scheme 2.

Scheme 1:

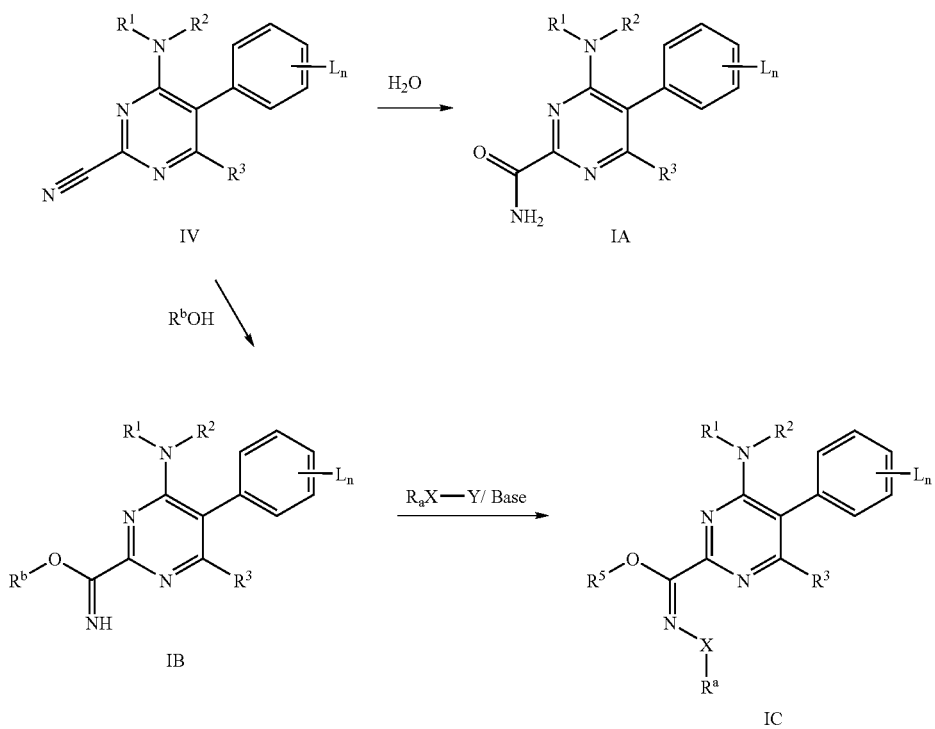

Scheme 2:

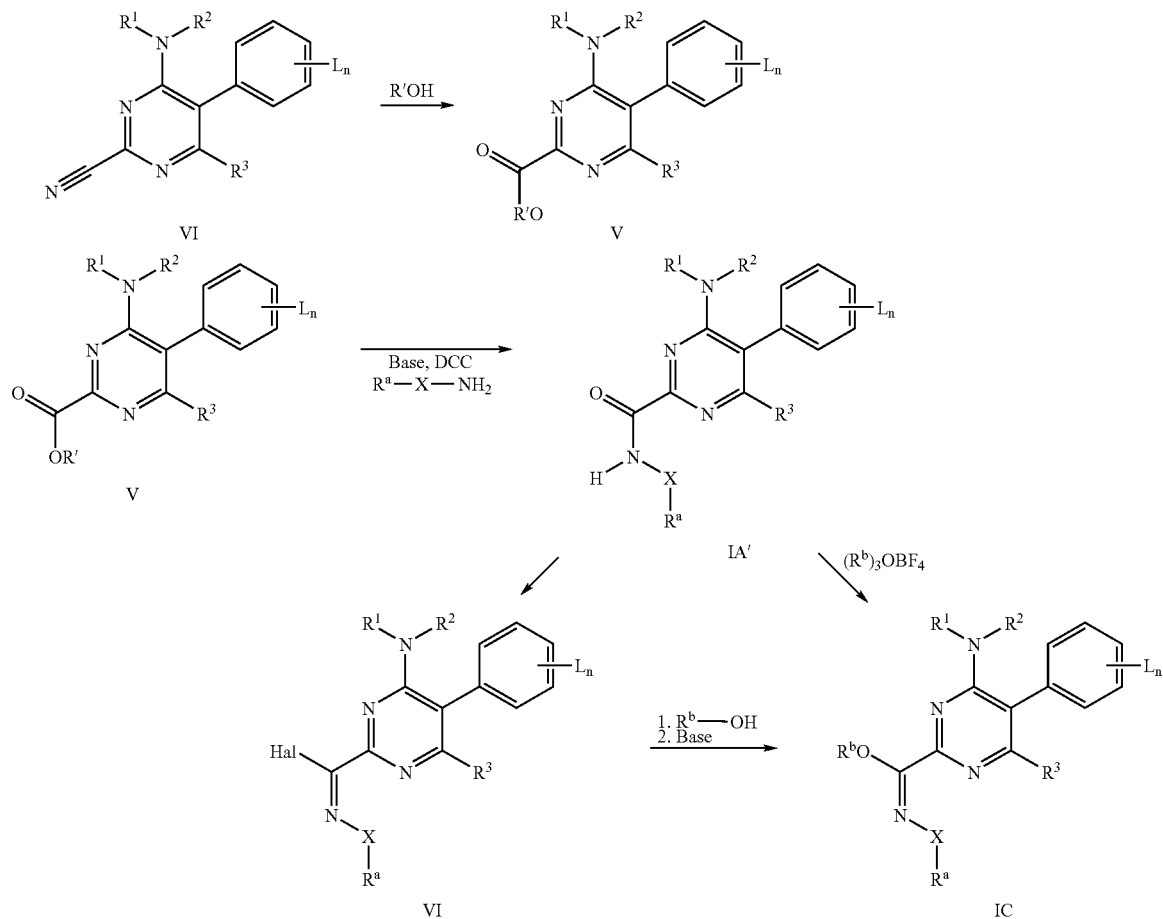

The synthesis, shown in Scheme 2, of the compounds IA' and IC in turn uses nitrile IV as starting material. The nitrile IV can preferably be prepared under acidic conditions in the presence of alcohols of the formula R'OH, where R' is $C_1$-$C_8$-alkyl, $C_2$-$C_8$-alkenyl, $C_2$-$C_8$-alkynyl or $C_3$-$C_6$-cycloalkyl, where the radicals alkyl, alkenyl and alkynyl may be partially or fully halogenated and may carry one to three groups $R^v$. The reaction of V with amines to give the amides IA' can be carried out as described in Org. Lett., 2001, Vol 3, p. 1053-56 or in J. Org. Chem., 2000, Vol 85, p. 8415-20. The subsequent reaction with Meerwein salts of the formula $(R^b)_3OBF_4$ analogously to the procedures given in Synth. Commun., 1983, 13, p. 753 or Helv. Chim. Acta, 1986, 69, p. 1224 yields the compounds of the formula IC according to the invention. The imine halides of the formula VI where Hal is halogen and in particular chlorine or bromine can be obtained analogously to Synthesis, 1991, Vol 9, p. 750-752. In an Appel reaction using, for example, carbon tetrabromide and triphenylphosphine, the corresponding bromine compounds are prepared. The latter can finally be reacted with alcohols of the formula $R^bOH$ and base to give the compounds IC according to the invention.

The radical $R^3$ (in particular alkyl) in the 6-position on the pyrimidine ring can be introduced by reaction with transition metal catalysis, such as Ni or Pd catalysis. In some cases it may be advisable to change the order and to introduce the substituent $R^3$ prior to the substituent $NR^1R^2$.

Scheme 3:

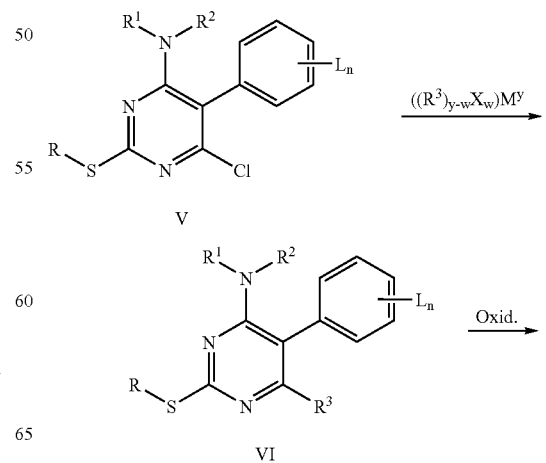

-continued

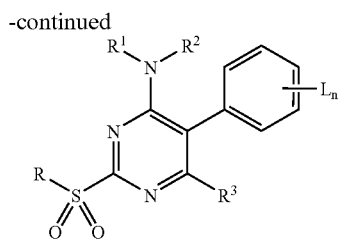

In the formula $(R^3)_{y-w}X_w\text{-}M^{y'}$, M is a metal ion of valency Y, such as, for example, B, Zn, Mg, Cu or Sn, X is chlorine, bromine, iodine or hydroxy, $R^3$ is preferably $C_1$-$C_4$-alkyl and w is a number from 0 to 3. This reaction can be carried out, for example, analogously to the following methods: J. Chem. Soc., Perkin Trans. 1 (1994), 1187, ibid.1 (1996), 2345; WO-A 99/41255; Aust. J. Chem. vol. 43 (1990), 733; J. Org. Chem. vol. 43 (1978), 358; J. Chem. Soc., Chem. Commun. (1979), 866; Tetrahedron Lett. vol. 34 (1993), 8267; ibid. vol. 33 (1992), 413.

The substituent $R^a$ in formula IA' can also be introduced as shown in Scheme 4.

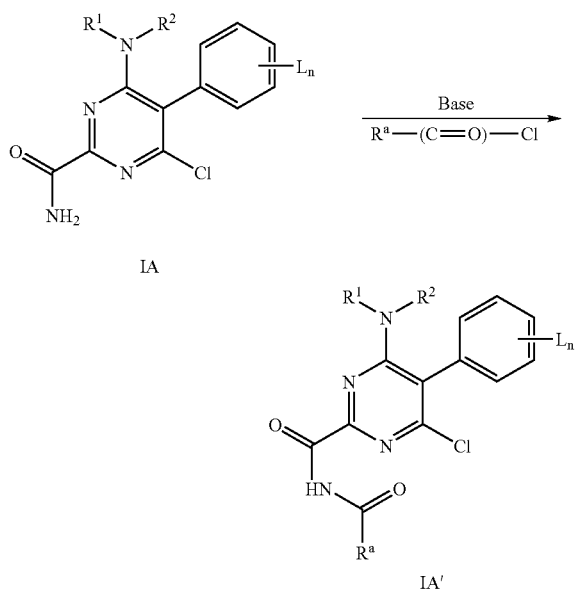

Here, the compounds of the formula IA are initially converted with the aid of strong bases into the anion and then reacted with the corresponding acid chlorides to give IA' (see J. Chem. Soc., Perkin Trans I, 1995, p. 3043). This gives compounds in which X is a C=O bridge. Bases suitable for preparing the anion are, for example, sodium amide and sodium hydride.

What was said above refers in particular to the preparation of compounds in which $R^3$ is an alkyl group. If $R^3$ is a cyano group or an alkoxy substituent, the radical $R^3$ can be introduced by reaction with alkali metal cyanides and alkali metal alkoxides, respectively.

In the definitions of the symbols given in the formulae above, collective terms were used which are generally representative for the following substituents:

halogen: fluorine, chlorine, bromine and iodine;
alkyl and the alkyl moieties of, for example, alkoxy, alkylamino, alkoxycarbonyl: saturated straight-chain or branched hydrocarbon radicals having 1 to 4, 6 or 8 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 8 carbon atoms (as mentioned above), where in these groups some or all of the hydrogen atoms may be replaced by halogen atoms as mentioned above, for example $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl;

alkenyl: unsaturated straight-chain or branched hydrocarbon radicals having 2 to 4, 6 or 8 carbon atoms and a double bond in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkadienyl: unsaturated straight-chain or branched hydrocarbon radicals having 4 or 6 carbon atoms and two double bonds in any position;

haloalkenyl: unsaturated straight-chain or branched hydrocarbon radicals having 2 to 6 carbon atoms and a double bond in any position (as mentioned above), where in these groups some or all of the hydrogen atoms may be replaced by halogen atoms as mentioned above, in particular by fluorine, chlorine and bromine;

alkynyl: straight-chain or branched hydrocarbon groups having 2 to 8 carbon atoms and a triple bond in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: mono- or bicyclic saturated hydrocarbon groups having 3 to 6 carbon ring members, for example $C_3$-$C_6$-cycloalkyl such as cyclopropyl, cyclobutyl, cyclopentyl, cyclohexyl;

five- or six-membered saturated, partially unsaturated or aromatic heterocycle which contains one to four heteroatoms from the group consisting of O, N and S:

5- or 6-membered heterocyclyl which contains one to three nitrogen atoms and/or one oxygen or sulfur atom or one or two oxygen and/or sulfur atoms, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

5-membered heteroaryl which contains one to four nitrogen atoms or one to three nitrogen atoms and one sulfur or oxygen atom: 5-membered heteroaryl groups which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered heteroaryl which contains one to three or one to four nitrogen atoms: 6-membered heteroaryl groups which, in addition to carbon atoms, may contain one to three and one to four nitrogen atoms, respectively, as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

a ring system which, if appropriate, is formed by $R^1$ und $R^2$ or by A and A' together with the nitrogen to which they are attached: pyrrolidine, morpholine, piperidine or tetrahydropyrazole.

The scope of the present invention includes the (R) and (S) isomers and the racemates of compounds of the formula I having chiral centers.

Hereinbelow, the embodiments of the invention are described in more detail.

With a view to the intended use of the pyrimidines of the formula I, particular preference is given to the following meanings of the substituents, in each case on their own or in combination:

Preference is given to compounds I in which $R^1$ is $C_1$-$C_6$-alkyl, $C_1$-$C_6$-haloalkyl, $C_2$-$C_6$-alkenyl, $C_2$-$C_6$-alkynyl or $C_3$-$C_6$-cycloalkyl and $R^2$ is hydrogen.

Especially preferred are compounds I in which $R^1$ is $C_1$-$C_6$-alkyl, $C_2$-$C_6$-alkenyl or $C_1$-$C_6$-haloalkyl branched in the α-position.

In addition, preference is given to compounds I in which $R^1$ is $C_1$-$C_4$-haloalkyl and $R^2$ is hydrogen.

Moreover, preference is given to compounds I in which $R^1$ and $R^2$ together with the nitrogen to which they are attached form a five- or six-membered ring which may be interrupted by an oxygen atom and may carry one or two $C_1$-$C_6$-alkyl substituents.

Especially preferred are groups $NR^1R^2$ such as—in particular in the α-position—methylated pyrrolidines or piperidines. Preference is furthermore given to 4-methylpiperidine.

Especially preferred are pyrimidines I in which the substituents $L^1$ to $L^5$ are as defined below:

L is halogen, cyano, $C_1$-$C_8$-alkyl, $C_1$-$C_6$-alkoxy, —C(=O)—O-A, —C(=O)—N(A')A, A, A', A" independently of one another are hydrogen, $C_1$-$C_6$-alkyl, $C_2$-$C_6$-alkenyl, $C_2$-$C_6$-alkynyl.

Moreover, preference is given to pyrimidines I where the phenyl group substituted by $L_n$ is the group B

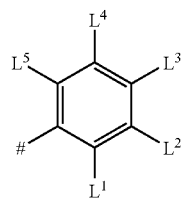

where # is the point of attachment to the pyrimidine skeleton and

- $L^1$ is fluorine, chlorine, $CH_3$ or $CF_3$;
- $L^2,L^4$ independently of one another are hydrogen, $CH_3$ or fluorine;
- $L^3$ is hydrogen, fluorine, chlorine, bromine, cyano, $CH_3$, $SCH_3$, $OCH_3$, $SO_2CH_3$, $CO-NH_2$, $CO-NHCH_3$, $CO-NHC_2H_5$, $CO-N(CH_3)_2$, $NH-C(=O)CH_3$, $N(CH_3)-C(=O)CH_3$ or $COOCH_3$ and
- $L^5$ is hydrogen, fluorine, chlorine or $CH_3$.

Particular preference is also given to compounds I in which $R^3$ is $C_1$-$C_4$-alkyl which may be substituted by halogen.

Moreover, particular preference is given to compounds I in which $R^3$ is halogen, cyano, $C_1$-$C_4$-alkyl or $C_1$-$C_4$-alkoxy.

Especially preferred are compounds I in which $R^3$ is methyl, cyano, methoxy or in particular chlorine.

Suitable with a view to their fungicidal action are pyrimidines of the formula I in which $R^4$ is

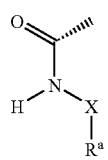 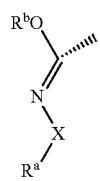

Preference is furthermore given to pyrimidines of the formula I in which $R^4$ is

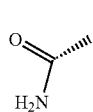 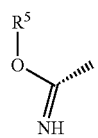

Especially preferred are pyrimidines of the formula I in which $R^4$ is

Finally, $R^4$ may preferably have the following meanings which may also be interpreted as definitions of prodrug radicals (see Medicinal Research Reviews 2003, 23, 763-793, or J. of Pharmaceutical Sciences 1997, 86, 765-767):

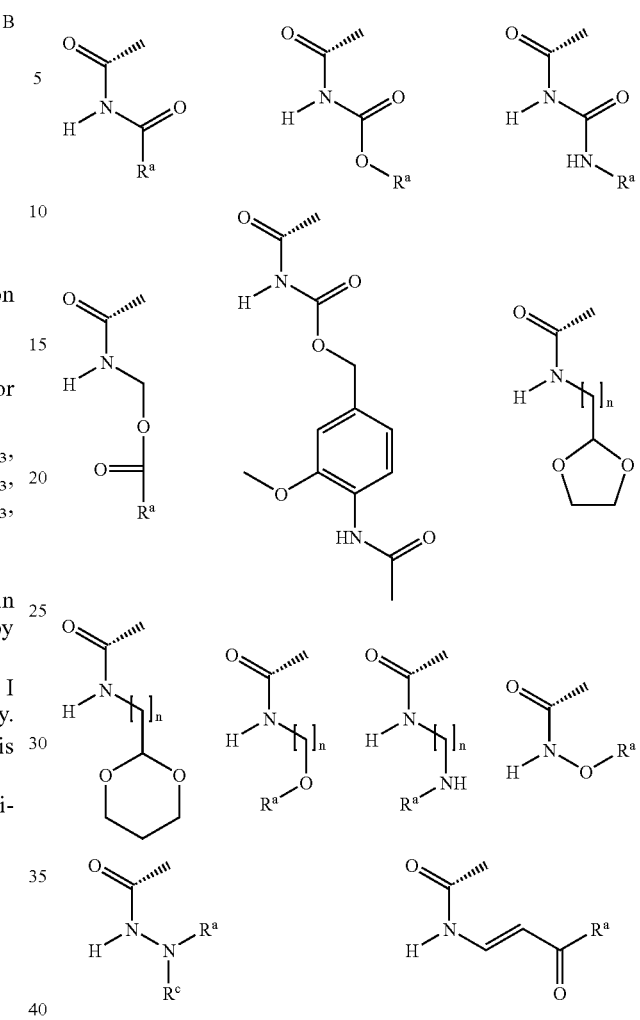

The index n in the alkenylene radicals of the above formulae is an integer from 1 to 3. Especially preferred are the following radical definitions $R^4$:

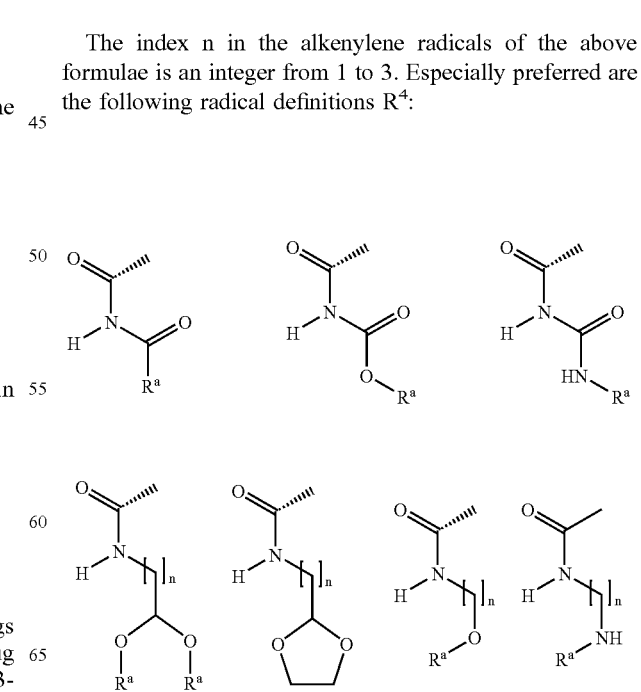

-continued

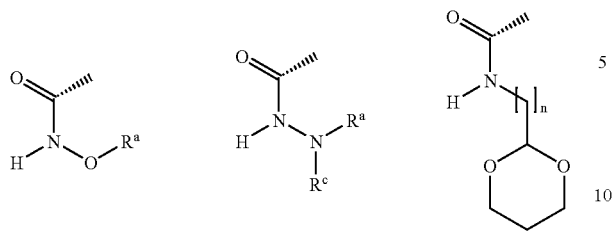

The bridge X is preferably a direct bond or —(C=O)—.

The substituent $R^a$ is preferably hydrogen, methyl, benzyl, trifluoromethyl, allyl, propargyl or methoxymethyl and particularly preferably hydrogen.

The substituent $R^b$ is preferably hydrogen, $C_1$-$C_6$-alkyl or $C_2$-$C_6$-alkenyl and particularly preferably: methyl, allyl or propargyl.

The substituent $R^c$ is preferably hydrogen or methyl.

The esters of the formula V

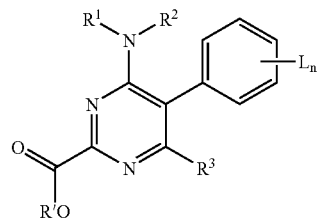

V are both interesting intermediates and excellent fungicidally active compounds.

The preferences in the definitions of $L_n$ and $R^1$ to $R^3$ mentioned above apply correspondingly to the esters of the formula V.

R' is in particular a $C_1$-$C_6$-alkyl radical, especially preferably an isopropyl radical.

However, R' may also have the meanings allyl, propargyl, benzyl, aminoalkyl, hydroxyalkyl, alkoxyalkyl or haloalkyl.

In particular with a view to their use, preference is given to compounds I and V compiled in the tables below. Moreover, the groups mentioned for a substituent in the tables are per se, independently of the combination in which they are mentioned, a particularly preferred embodiment of the substituent in question.

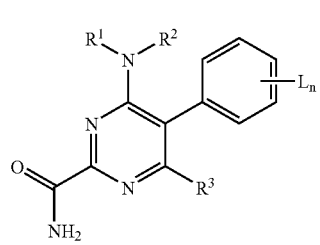

Ia

-continued

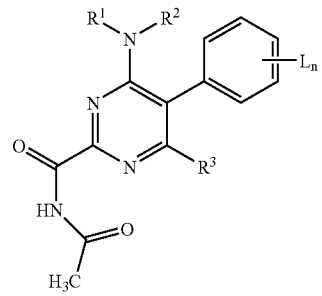

Ib

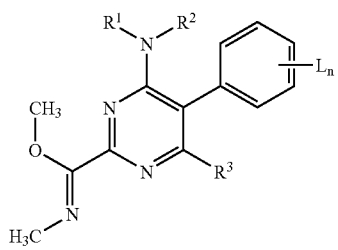

Ic

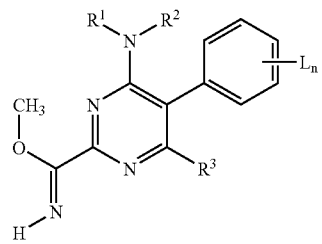

Id

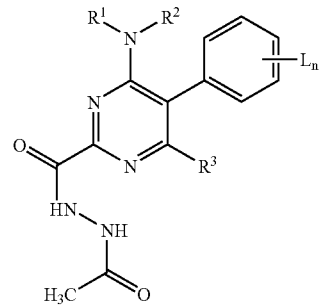

Ie

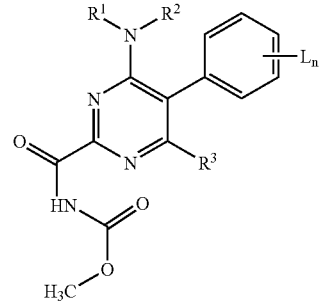

If

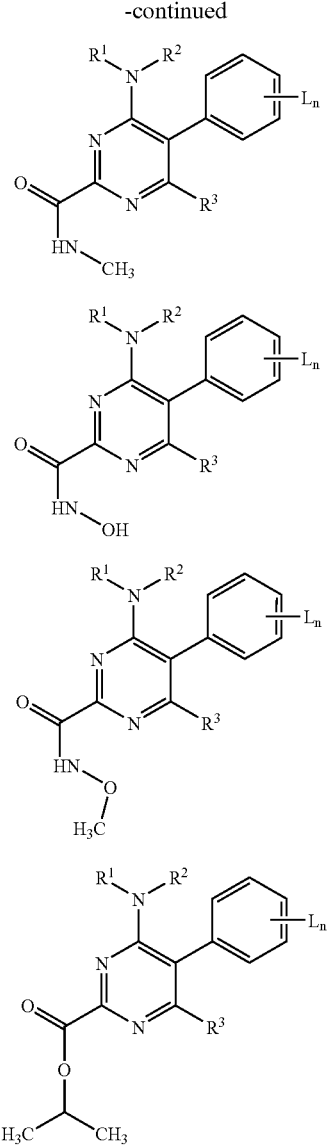

Table 1
Compounds of the formulae Ia, Ib, Ic, Id, Ie, If, Ig, Ih, Ii and Va in which $L_n$ is 2-fluoro-6-chloro, $R^3$ is methyl and $R^1$, $R^2$ for a compound correspond in each case to one row of Table A Table 2
Compounds of the formulae Ia, Ib, Ic, Id, Ie, If, Ig, Ih, Ii and Va in which $L_n$ is 2,6-difluoro, $R^3$ is methyl and $R^1$, $R^2$ for a compound correspond in each case to one row of Table A Table 3
Compounds of the formulae Ia, Ib, Ic, Id, Ie, If, Ig, Ih, Ii and Va in which $L_n$ is 2,6-dichloro, $R^3$ is methyl and $R^1$, $R^2$ for a compound correspond in each case to one row of Table A Table 4
Compounds of the formulae Ia, Ib, Ic, Id, Ie, If, Ig, Ih, Ii and Va in which $L_n$ is 2-fluoro-6-methyl, $R^3$ is methyl and $R^1$, $R^2$ for a compound correspond in each case to one row of Table A Table 5
Compounds of the formulae Ia, Ib, Ic, Id, Ie, If, Ig, Ih, Ii and Va in which $L_n$ is 2,4,6-trifluoro, $R^3$ is methyl and $R^1$, $R^2$ for a compound correspond in each case to one row of Table A Table 6
Compounds of the formulae Ia, Ib, Ic, Id, Ie, If, Ig, Ih, Ii and Va in which $L_n$ is 2-methyl-4-fluoro, $R^3$ is methyl and $R^1$, $R^2$ for a compound correspond in each case to one row of Table A Table 7
Compounds of the formulae Ia, Ib, Ic, Id, Ie, If, Ig, Ih, Ii and Va in which $L_n$ is 2-fluoro-4-methoxycarbonyl, $R^3$ is methyl and $R^1$, $R^2$ for a compound correspond in each case to one row of Table A Table 8
Compounds of the formulae Ia, Ib, Ic, Id, Ie, If, Ig, Ih, Ii and Va in which $L_n$ is 2-fluoro-4-CN, $R^3$ is methyl and $R^1$, $R^2$ for a compound correspond in each case to one row of Table A Table 9
Compounds of the formulae Ia, Ib, Ic, Id, Ie, If, Ig, Ih, Ii and Va in which $L_n$ is 2,4,5-trifluoro, $R^3$ is methyl and $R^1$, $R^2$ for a compound correspond in each case to one row of Table A Table 10
Compounds of the formulae Ia, Ib, Ic, Id, Ie, If, Ig, Ih, Ii and Va in which $L_n$ is 2,4-dichloro, $R^3$ is methyl and $R^1$, $R^2$ for a compound correspond in each case to one row of Table A Table 11
Compounds of the formulae Ia, Ib, Ic, Id, Ie, If, Ig, Ih, Ii and Va in which $L_n$ is 2-chloro, $R^3$ is methyl and $R^1$, $R^2$ for a compound correspond in each case to one row of Table A Table 12
Compounds of the formulae Ia, Ib, Ic, Id, Ie, If, Ig, Ih, Ii and Va in which $L_n$ is 2-fluoro, $R^3$ is methyl and $R^1$, $R^2$ for a compound correspond in each case to one row of Table A Table 13
Compounds of the formulae Ia, Ib, Ic, Id, Ie, If, Ig, Ih, Ii and Va in which $L_n$ is 2,4-difluoro, $R^3$ is methyl and $R^1$, $R^2$ for a compound correspond in each case to one row of Table A Table 14
Compounds of the formulae Ia, Ib, Ic, Id, Ie, If, Ig, Ih, Ii and Va in which $L_n$ is 2-fluoro-4-chloro, $R^3$ is methyl and $R^1$, $R^2$ for a compound correspond in each case to one row of Table A Table 15
Compounds of the formulae Ia, Ib, Ic, Id, Ie, If, Ig, Ih, Ii and Va in which $L_n$ is 2-chloro-4-fluoro, $R^3$ is methyl and $R^1$, $R^2$ for a compound correspond in each case to one row of Table A Table 16
Compounds of the formulae Ia, Ib, Ic, Id, Ie, If, Ig, Ih, Ii and Va in which $L_n$ is 2,3-difluoro, $R^3$ is methyl and $R^1$, $R^2$ for a compound correspond in each case to one row of Table A Table 17
Compounds of the formulae Ia, Ib, Ic, Id, Ie, If, Ig, Ih, Ii and Va in which $L_n$ is 2,5-difluoro, $R^3$ is methyl and $R^1$, $R^2$ for a compound correspond in each case to one row of Table A Table 18
Compounds of the formulae Ia, Ib, Ic, Id, Ie, If, Ig, Ih, Ii and Va in which $L_n$ is 2,3,4-trifluoro, $R^3$ is methyl and $R^1$, $R^2$ for a compound correspond in each case to one row of Table A Table 19
Compounds of the formulae Ia, Ib, Ic, Id, Ie, If, Ig, Ih, Ii and Va in which $L_n$ is 2-methyl, $R^3$ is methyl and $R^1$, $R^2$ for a compound correspond in each case to one row of Table A Table 20
Compounds of the formulae Ia, Ib, Ic, Id, Ie, If, Ig, Ih, Ii and Va in which $L_n$ is 2,4-dimethyl, $R^3$ is methyl and $R^1$, $R^2$ for a compound correspond in each case to one row of Table A Table 21
Compounds of the formulae Ia, Ib, Ic, Id, Ie, If, Ig, Ih, Ii and Va in which $L_n$ is 2-methyl-4-chloro, $R^3$ is methyl and $R^1$, $R^2$ for a compound correspond in each case to one row of Table A Table 22
Compounds of the formulae Ia, Ib, Ic, Id, Ie, If, Ig, Ih, Ii and Va in which $L_n$ is 2-fluoro-4-methyl, $R^3$ is methyl and $R^1$, $R^2$ for a compound correspond in each case to one row of Table A Table 23
Compounds of the formulae Ia, Ib, Ic, Id, Ie, If, Ig, Ih, Ii and Va in which $L_n$ is 2,6-dimethyl, $R^3$ is methyl and $R^1$, $R^2$ for a compound correspond in each case to one row of Table A Table 24
Compounds of the formulae Ia, Ib, Ic, Id, Ie, If, Ig, Ih, Ii and Va in which $L_n$ is 2,4,6-trimethyl, $R^3$ is methyl and $R^1$, $R^2$ for a compound correspond in each case to one row of Table A Table 25
Compounds of the formulae Ia, Ib, Ic, Id, Ie, If, Ig, Ih, Ii and Va in which $L_n$ is 2,6-difluoro-4-cyano, $R^3$ is methyl and $R^1$, $R^2$ for a compound correspond in each case to one row of Table A Table 26
Compounds of the formulae Ia, Ib, Ic, Id, Ie, If, Ig, Ih, Ii and Va in which $L_n$ is 2,6-difluoro-4-methyl, $R^3$ is methyl and $R^1$, $R^2$ for a compound correspond in each case to one row of Table A Table 27
Compounds of the formulae Ia, Ib, Ic, Id, Ie, If, Ig, Ih, Ii and Va in which $L_n$ is 2,6-difluoro-4-methoxycarbonyl, $R^3$ is methyl and $R^1$, $R^2$ for a compound correspond in each case to one row of Table A Table 28
Compounds of the formulae Ia, Ib, Ic, Id, Ie, If, Ig, Ih, Ii and Va in which $L_n$ is 2-chloro, 4-methoxy, $R^3$ is methyl and $R^1$, $R^2$ for a compound correspond in each case to one row of Table A Table 29
Compounds of the formulae Ia, Ib, Ic, Id, Ie, If, Ig, Ih, Ii and Va in which $L_n$ is 2-chloro, 4-methyl, $R^3$ is methyl and $R^1$, $R^2$ for a compound correspond in each case to one row of Table A Table 30
Compounds of the formulae Ia, Ib, Ic, Id, Ie, If, Ig, Ih, Ii and Va in which $L_n$ is 2-chloro, 4-methoxycarbonyl, $R^3$ is methyl and $R^1$, $R^2$ for a compound correspond in each case to one row of Table A Table 31
Compounds of the formulae Ia, Ib, Ic, Id, Ie, If, Ig, Ih, Ii and Va in which $L_n$ is 2-chloro, 4-bromo, $R^3$ is methyl and $R^1$, $R^2$ for a compound correspond in each case to one row of Table A Table 32
Compounds of the formulae Ia, Ib, Ic, Id, Ie, If, Ig, Ih, Ii and Va in which $L_n$ is 2-chloro, 4-cyano, $R^3$ is methyl and $R^1$, $R^2$ for a compound correspond in each case to one row of Table A Table 33
Compounds of the formulae Ia, Ib, Ic, Id, Ie, If, Ig, Ih, Ii and Va in which $L_n$ is 2,6-difluoro, 4-methoxy, $R^3$ is methyl and $R^1$, $R^2$ for a compound correspond in each case to one row of Table A Table 34
Compounds of the formulae Ia, Ib, Ic, Id, Ie, If, Ig, Ih, Ii and Va in which $L_n$ is 2-fluoro, 3-methyl, $R^3$ is methyl and $R^1$, $R^2$ for a compound correspond in each case to one row of Table A Table 35
Compounds of the formulae Ia, Ib, Ic, Id, Ie, If, Ig, Ih, Ii and Va in which $L_n$ is 2,5-dimethyl, $R^3$ is methyl and $R^1$, $R^2$ for a compound correspond in each case to one row of Table A Table 36
Compounds of the formulae Ia, Ib, Ic, Id, Ie, If, Ig, Ih, Ii and Va in which $L_n$ is 2-methyl, 4-cyano, $R^3$ is methyl and $R^1$, $R^2$ for a compound correspond in each case to one row of Table A Table 37
Compounds of the formulae Ia, Ib, Ic, Id, Ie, If, Ig, Ih, Ii and Va in which $L_n$ is 2-methyl, 4-bromo, $R^3$ is methyl and $R^1$, $R^2$ for a compound correspond in each case to one row of Table A Table 38
Compounds of the formulae Ia, Ib, Ic, Id, Ie, If, Ig, Ih, Ii and Va in which $L_n$ is 2-methyl, 5-fluoro, $R^3$ is methyl and $R^1$, $R^2$ for a compound correspond in each case to one row of Table A Table 39
Compounds of the formulae Ia, Ib, Ic, Id, Ie, If, Ig, Ih, Ii and Va in which $L_n$ is 2-methyl, 4-methoxy, $R^3$ is methyl and $R^1$, $R^2$ for a compound correspond in each case to one row of Table A Table 40
Compounds of the formulae Ia, Ib, Ic, Id, Ie, If, Ig, Ih, Ii and Va in which $L_n$ is 2-methyl, 4-methoxycarbonyl, $R^3$ is methyl and $R^1$, $R^2$ for a compound correspond in each case to one row of Table A Table 41
Compounds of the formulae Ia, Ib, Ic, Id, Ie, If, Ig, Ih, Ii and Va in which $L_n$ is 2,5-dimethyl, 4-bromo, $R^3$ is methyl and $R^1$, $R^2$ for a compound correspond in each case to one row of Table A Table 42
Compounds of the formulae Ia, Ib, Ic, Id, Ie, If, Ig, Ih, Ii and Va in which $L_n$ is 2-fluoro, 4-bromo, $R^3$ is methyl and $R^1$, $R^2$ for a compound correspond in each case to one row of Table A Table 43
Compounds of the formulae Ia, Ib, Ic, Id, Ie, If, Ig, Ih, Ii and Va in which $L_n$ is 2-fluoro, 4-methoxy, $R^3$ is methyl and $R^1$, $R^2$ for a compound correspond in each case to one row of Table A Table 44
Compounds of the formulae Ia, Ib, Ic, Id, Ie, If, Ig, Ih, Ii and Va in which $L_n$ is 2-fluoro, 5-methyl, $R^3$ is methyl and $R^1$, $R^2$ for a compound correspond in each case to one row of Table A Table 45
Compounds of the formulae Ia, Ib, Ic, Id, Ie, If, Ig, Ih, Ii and Va in which $L_n$ is pentafluoro, $R^3$ is methyl and $R^1$, $R^2$ for a compound correspond in each case to one row of Table A Table 46
Compounds of the formulae Ia, Ib, Ic, Id, Ie, If, Ig, Ih, Ii and Va in which $L_n$ is 2-fluoro, 6-chloro, $R^3$ is chloro and $R^1$, $R^2$ for a compound correspond in each case to one row of Table A Table 47
Compounds of the formulae Ia, Ib, Ic, Id, Ie, If, Ig, Ih, Ii and Va in which $L_n$ is 2,6-difluoro, $R^3$ is chloro and $R^1$, $R^2$ for a compound correspond in each case to one row of Table A Table 48
Compounds of the formulae Ia, Ib, Ic, Id, Ie, If, Ig, Ih, Ii and Va in which $L_n$ is 2,6-dichloro, $R^3$ is chloro and $R^1$, $R^2$ for a compound correspond in each case to one row of Table A Table 49
Compounds of the formulae Ia, Ib, Ic, Id, Ie, If, Ig, Ih, Ii and Va in which $L_n$ is 2-fluoro, 6-methyl, $R^3$ is chloro and $R^1$, $R^2$ for a compound correspond in each case to one row of Table A Table 50
Compounds of the formulae Ia, Ib, Ic, Id, Ie, If, Ig, Ih, Ii and Va in which $L_n$ is 2,4,6-trifluoro, $R^3$ is chloro and $R^1$, $R^2$ for a compound correspond in each case to one row of Table A Table 51
Compounds of the formulae Ia, Ib, Ic, Id, Ie, If, Ig, Ih, Ii and Va in which $L_n$ is 2-methyl, 4-fluoro, $R^3$ is chloro and $R^1$, $R^2$ for a compound correspond in each case to one row of Table A Table 52
Compounds of the formulae Ia, Ib, Ic, Id, Ie, If, Ig, Ih, Ii and Va in which $L_n$ is 2-fluoro, 4-methoxycarbonyl, $R^3$ is chloro and $R^1$, $R^2$ for a compound correspond in each case to one row of Table A Table 53
Compounds of the formulae Ia, Ib, Ic, Id, Ie, If, Ig, Ih, Ii and Va in which $L_n$ is 2-fluoro, 4-CN, $R^3$ is chloro and $R^1$, $R^2$ for a compound correspond in each case to one row of Table A Table 54
Compounds of the formulae Ia, Ib, Ic, Id, Ie, If, Ig, Ih, Ii and Va in which $L_n$ is 2,4,5-trifluoro, $R^3$ is chloro and $R^1$, $R^2$ for a compound correspond in each case to one row of Table A Table 55
Compounds of the formulae Ia, Ib, Ic, Id, Ie, If, Ig, Ih, Ii and Va in which $L_n$ is 2,4-dichloro, $R^3$ is chloro and $R^1$, $R^2$ for a compound correspond in each case to one row of Table A 56
Compounds of the formulae Ia, Ib, Ic, Id, Ie, If, Ig, Ih, Ii and Va in which $L_n$ is 2-chloro, $R^3$ is chloro and $R^1$, $R^2$ for a compound correspond in each case to one row of Table A Table 57
Compounds of the formulae Ia, Ib, Ic, Id, Ie, If, Ig, Ih, Ii and Va in which $L_n$ is 2-fluoro, $R^3$ is chloro and $R^1$, $R^2$ for a compound correspond in each case to one row of Table A Table 58
Compounds of the formulae Ia, Ib, Ic, Id, Ie, If, Ig, Ih, Ii and Va in which $L_n$ is 2,4-difluoro, $R^3$ is chloro and $R^1$, $R^2$ for a compound correspond in each case to one row of Table A Table 59
Compounds of the formulae Ia, Ib, Ic, Id, Ie, If, Ig, Ih, Ii and Va in which $L_n$ is 2-fluoro-4-chloro, $R^3$ is chloro and $R^1$, $R^2$ for a compound correspond in each case to one row of Table A Table 60
Compounds of the formulae Ia, Ib, Ic, Id, Ie, If, Ig, Ih, Ii and Va in which $L_n$ is 2-chloro-4-fluoro, $R^3$ is chloro and $R^1$, $R^2$ for a compound correspond in each case to one row of Table A Table 61
Compounds of the formulae Ia, Ib, Ic, Id, Ie, If, Ig, Ih, Ii and Va in which $L_n$ is 2,3-difluoro, $R^3$ is chloro and $R^1$, $R^2$ for a compound correspond in each case to one row of Table A Table 62
Compounds of the formulae Ia, Ib, Ic, Id, Ie, If, Ig, Ih, Ii and Va in which $L_n$ is 2,5-difluoro, $R^3$ is chloro and $R^1$, $R^2$ for a compound correspond in each case to one row of Table A Table 63
Compounds of the formulae Ia, Ib, Ic, Id, Ie, If, Ig, Ih, Ii and Va in which $L_n$ is 2,3,4-trifluoro, $R^3$ is chloro and $R^1$, $R^2$ for a compound correspond in each case to one row of Table A Table 64
Compounds of the formulae Ia, Ib, Ic, Id, Ie, If, Ig, Ih, Ii and Va in which $L_n$ is 2-methyl, $R^3$ is chloro and $R^1$, $R^2$ for a compound correspond in each case to one row of Table A Table 65
Compounds of the formulae Ia, Ib, Ic, Id, Ie, If, Ig, Ih, Ii and Va in which $L_n$ is 2,4-dimethyl, $R^3$ is chloro and $R^1$, $R^2$ for a compound correspond in each case to one row of Table A Table 66
Compounds of the formulae Ia, Ib, Ic, Id, Ie, If, Ig, Ih, Ii and Va in which $L_n$ is 2-methyl-4-chloro, $R^3$ is chloro and $R^1$, $R^2$ for a compound correspond in each case to one row of Table A Table 67
Compounds of the formulae Ia, Ib, Ic, Id, Ie, If, Ig, Ih, Ii and Va in which $L_n$ is 2-fluoro-4-methyl, $R^3$ is chloro and $R^1$, $R^2$ for a compound correspond in each case to one row of Table A Table 68
Compounds of the formulae Ia, Ib, Ic, Id, Ie, If, Ig, Ih, Ii and Va in which $L_n$ is 2,6-dimethyl, $R^3$ is chloro and $R^1$, $R^2$ for a compound correspond in each case to one row of Table A Table 69
Compounds of the formulae Ia, Ib, Ic, Id, Ie, If, Ig, Ih, Ii and Va in which $L_n$ is 2,4,6-trimethyl, $R^3$ is chloro and $R^1$, $R^2$ for a compound correspond in each case to one row of Table A Table 70
Compounds of the formulae Ia, Ib, Ic, Id, Ie, If, Ig, Ih, Ii and Va in which $L_n$ is 2,6-difluoro-4-cyano, $R^3$ is chloro and $R^1$, $R^2$ for a compound correspond in each case to one row of Table A Table 71
Compounds of the formulae Ia, Ib, Ic, Id, Ie, If, Ig, Ih, Ii and Va in which $L_n$ is 2,6-difluoro-4-methyl, $R^3$ is chloro and $R^1$, $R^2$ for a compound correspond in each case to one row of Table A Table 72
Compounds of the formulae Ia, Ib, Ic, Id, Ie, If, Ig, Ih, Ii and Va in which $L_n$ is 2,6-difluoro-4-methoxycarbonyl, $R^3$ is chloro and $R^1$, $R^2$ for a compound correspond in each case to one row of Table A Table 73
Compounds of the formulae Ia, Ib, Ic, Id, Ie, If, Ig, Ih, Ii and Va in which $L_n$ is 2-chloro, 4-methoxy, $R^3$ is chloro and $R^1$, $R^2$ for a compound correspond in each case to one row of Table A Table 74
Compounds of the formulae Ia, Ib, Ic, Id, Ie, If, Ig, Ih, Ii and Va in which $L_n$ is 2-chloro, 4-methyl, $R^3$ is chloro and $R^1$, $R^2$ for a compound correspond in each case to one row of Table A Table 75
Compounds of the formulae Ia, Ib, Ic, Id, Ie, If, Ig, Ih, Ii and Va in which $L_n$ is 2-chloro, 4-methoxycarbonyl, $R^3$ is chloro and $R^1$, $R^2$ for a compound correspond in each case to one row of Table A Table 76
Compounds of the formulae Ia, Ib, Ic, Id, Ie, If, Ig, Ih, Ii and Va in which $L_n$ is 2-chloro, 4-bromo, $R^3$ is chloro and $R^1$, $R^2$ for a compound correspond in each case to one row of Table A Table 77
Compounds of the formulae Ia, Ib, Ic, Id, Ie, If, Ig, Ih, Ii and Va in which $L_n$ is 2-chloro, 4-cyano, $R^3$ is chloro and $R^1$, $R^2$ for a compound correspond in each case to one row of Table A Table 78
Compounds of the formulae Ia, Ib, Ic, Id, Ie, If, Ig, Ih, Ii and Va in which $L_n$ is 2,6-difluoro, 4-methoxy, $R^3$ is chloro and $R^1$, $R^2$ for a compound correspond in each case to one row of Table A Table 79
Compounds of the formulae Ia, Ib, Ic, Id, Ie, If, Ig, Ih, Ii and Va in which $L_n$ is 2-fluoro, 3-methyl, $R^3$ is chloro and $R^1$, $R^2$ for a compound correspond in each case to one row of Table A Table 80
Compounds of the formulae Ia, Ib, Ic, Id, Ie, If, Ig, Ih, Ii and Va in which $L_n$ is 2,5-dimethyl, $R^3$ is chloro and $R^1$, $R^2$ for a compound correspond in each case to one row of Table A Table 81
Compounds of the formulae Ia, Ib, Ic, Id, Ie, If, Ig, Ih, Ii and Va in which $L_n$ is 2-methyl, 4-cyano, $R^3$ is chloro and $R^1$, $R^2$ for a compound correspond in each case to one row of Table A Table 82
Compounds of the formulae Ia, Ib, Ic, Id, Ie, If, Ig, Ih, Ii and Va in which $L_n$ is 2-methyl, 4-bromo, $R^3$ is chloro and $R^1$, $R^2$ for a compound correspond in each case to one row of Table A Table 83
Compounds of the formulae Ia, Ib, Ic, Id, Ie, If, Ig, Ih, Ii and Va in which $L_n$ is 2-methyl, 5-fluoro, $R^3$ is chloro and $R^1$, $R^2$ for a compound correspond in each case to one row of Table A Table 84
Compounds of the formulae Ia, Ib, Ic, Id, Ie, If, Ig, Ih, Ii and Va in which $L_n$ is 2-methyl, 4-methoxy, $R^3$ is chloro and $R^1$, $R^2$ for a compound correspond in each case to one row of Table A Table 85
Compounds of the formulae Ia, Ib, Ic, Id, Ie, If, Ig, Ih, Ii and Va in which $L_n$ is 2-methyl, 4-methoxycarbonyl, $R^3$ is chloro and $R^1$, $R^2$ for a compound correspond in each case to one row of Table A Table 86
Compounds of the formulae Ia, Ib, Ic, Id, Ie, If, Ig, Ih, Ii and Va in which $L_n$ is 2,5-dimethyl, 4-bromo, $R^3$ is chloro and $R^1$, $R^2$ for a compound correspond in each case to one row of Table A Table 87
Compounds of the formulae Ia, Ib, Ic, Id, Ie, If, Ig, Ih, Ii and Va in which $L_n$ is 2-fluoro, 4-bromo, $R^3$ is chloro and $R^1$, $R^2$ for a compound correspond in each case to one row of Table A Table 88
Compounds of the formulae Ia, Ib, Ic, Id, Ie, If, Ig, Ih, Ii and Va in which $L_n$ is 2-fluoro, 4-methoxy, $R^3$ is chloro and $R^1$, $R^2$ for a compound correspond in each case to one row of Table A Table 89
Compounds of the formulae Ia, Ib, Ic, Id, Ie, If, Ig, Ih, Ii and Va in which $L_n$ is 2-fluoro, 5-methyl, $R^3$ is chloro and $R^1$, $R^2$ for a compound correspond in each case to one row of Table A Table 90
Compounds of the formulae Ia, Ib, Ic, Id, Ie, If, Ig, Ih, Ii and Va in which $L_n$ is pentafluoro, $R^3$ is chloro and $R^1$, $R^2$ for a compound correspond in each case to one row of Table A Table 91
Compounds of the formulae Ia, Ib, Ic, Id, Ie, If, Ig, Ih, Ii and Va in which $L_n$ is 2-fluoro, 6-chloro, $R^3$ is methoxy and $R^1$, $R^2$ for a compound correspond in each case to one row of Table A Table 92
Compounds of the formulae Ia, Ib, Ic, Id, Ie, If, Ig, Ih, Ii and Va in which $L_n$ is 2,6-difluoro, $R^3$ is methoxy and $R^1$, $R^2$ for a compound correspond in each case to one row of Table A Table 93
Compounds of the formulae Ia, Ib, Ic, Id, Ie, If, Ig, Ih, Ii and Va in which $L_n$ is 2,6-dichloro, $R^3$ is methoxy and $R^1$, $R^2$ for a compound correspond in each case to one row of Table A Table 94
Compounds of the formulae Ia, Ib, Ic, Id, Ie, If, Ig, Ih, Ii and Va in which $L_n$ is 2-fluoro, 6-methyl, $R^3$ is methoxy and $R^1$, $R^2$ for a compound correspond in each case to one row of Table A Table 95
Compounds of the formulae Ia, Ib, Ic, Id, Ie, If, Ig, Ih, Ii and Va in which $L_n$ is 2,4,6-trifluoro, $R^3$ is methoxy and $R^1$, $R^2$ for a compound correspond in each case to one row of Table A Table 96
Compounds of the formulae Ia, Ib, Ic, Id, Ie, If, Ig, Ih, Ii and Va in which $L_n$ is 2-methyl, 4-fluoro, $R^3$ is methoxy and $R^1$, $R^2$ for a compound correspond in each case to one row of Table A Table 97
Compounds of the formulae Ia, Ib, Ic, Id, Ie, If, Ig, Ih, Ii and Va in which $L_n$ is 2-fluoro, 4-methoxycarbonyl, $R^3$ is methoxy and $R^1$, $R^2$ for a compound correspond in each case to one row of Table A Table 98
Compounds of the formulae Ia, Ib, Ic, Id, Ie, If, Ig, Ih, Ii and Va in which $L_n$ is 2-fluoro, 4-CN, $R^3$ is methoxy and $R^1$, $R^2$ for a compound correspond in each case to one row of Table A Table 99
Compounds of the formulae Ia, Ib, Ic, Id, Ie, If, Ig, Ih, Ii and Va in which $L_n$ is 2,4,5-trifluoro, $R^3$ is methoxy and $R^1$, $R^2$ for a compound correspond in each case to one row of Table A Table 100
Compounds of the formulae Ia, Ib, Ic, Id, Ie, If, Ig, Ih, Ii and Va in which $L_n$ is 2,4-dichloro, $R^3$ is methoxy and $R^1$, $R^2$ for a compound correspond in each case to one row of Table A Table 101
Compounds of the formulae Ia, Ib, Ic, Id, Ie, If, Ig, Ih, Ii and Va in which $L_n$ is 2-chloro, $R^3$ is methoxy and $R^1$, $R^2$ for a compound correspond in each case to one row of Table A Table 102
Compounds of the formulae Ia, Ib, Ic, Id, Ie, If, Ig, Ih, Ii and Va in which $L_n$ is 2-fluoro, $R^3$ is methoxy and $R^1$, $R^2$ for a compound correspond in each case to one row of Table A Table 103
Compounds of the formulae Ia, Ib, Ic, Id, Ie, If, Ig, Ih, Ii and Va in which $L_n$ is 2,4-difluoro, $R^3$ is methoxy and $R^1$, $R^2$ for a compound correspond in each case to one row of Table A Table 104
Compounds of the formulae Ia, Ib, Ic, Id, Ie, If, Ig, Ih, Ii and Va in which $L_n$ is 2-fluoro-4-chloro, $R^3$ is methoxy and $R^1$, $R^2$ for a compound correspond in each case to one row of Table A Table 105
Compounds of the formulae Ia, Ib, Ic, Id, Ie, If, Ig, Ih, Ii and Va in which $L_n$ is 2-chloro-4-fluoro, $R^3$ is methoxy and $R^1$, $R^2$ for a compound correspond in each case to one row of Table A Table 106
Compounds of the formulae Ia, Ib, Ic, Id, Ie, If, Ig, Ih, Ii and Va in which $L_n$ is 2,3-difluoro, $R^3$ is methoxy and $R^1$, $R^2$ for a compound correspond in each case to one row of Table A Table 107
Compounds of the formulae Ia, Ib, Ic, Id, Ie, If, Ig, Ih, Ii and Va in which $L_n$ is 2,5-difluoro, $R^3$ is methoxy and $R^1$, $R^2$ for a compound correspond in each case to one row of Table A Table 108
Compounds of the formulae Ia, Ib, Ic, Id, Ie, If, Ig, Ih, Ii and Va in which $L_n$ is 2,3,4-trifluoro, $R^3$ is methoxy and $R^1$, $R^2$ for a compound correspond in each case to one row of Table A Table 109
Compounds of the formulae Ia, Ib, Ic, Id, Ie, If, Ig, Ih, Ii and Va in which $L_n$ is 2-methyl, $R^3$ is methoxy and $R^1$, $R^2$ for a compound correspond in each case to one row of Table A Table 110
Compounds of the formulae Ia, Ib, Ic, Id, Ie, If, Ig, Ih, Ii and Va in which $L_n$ is 2,4-dimethyl, $R^3$ is methoxy and $R^1$, $R^2$ for a compound correspond in each case to one row of Table A Table 111
Compounds of the formulae Ia, Ib, Ic, Id, Ie, If, Ig, Ih, Ii and Va in which $L_n$ is 2-methyl-4-chloro, $R^3$ is methoxy and $R^1$, $R^2$ for a compound correspond in each case to one row of Table A Table 112
Compounds of the formulae Ia, Ib, Ic, Id, Ie, If, Ig, Ih, Ii and Va in which $L_n$ is 2-fluoro-4-methyl, $R^3$ is methoxy and $R^1$, $R^2$ for a compound correspond in each case to one row of Table A Table 113
Compounds of the formulae Ia, Ib, Ic, Id, Ie, If, Ig, Ih, Ii and Va in which $L_n$ is 2,6-dimethyl, $R^3$ is methoxy and $R^1$, $R^2$ for a compound correspond in each case to one row of Table A Table 114
Compounds of the formulae Ia, Ib, Ic, Id, Ie, If, Ig, Ih, Ii and Va in which $L_n$ is 2,4,6-trimethyl, $R^3$ is methoxy and $R^1$, $R^2$ for a compound correspond in each case to one row of Table A Table 115
Compounds of the formulae Ia, Ib, Ic, Id, Ie, If, Ig, Ih, Ii and Va in which $L_n$ is 2,6-difluoro-4-cyano, $R^3$ is methoxy and $R^1$, $R^2$ for a compound correspond in each case to one row of Table A Table 116
Compounds of the formulae Ia, Ib, Ic, Id, Ie, If, Ig, Ih, Ii and Va in which $L_n$ is 2,6-difluoro-4-methyl, $R^3$ is methoxy and $R^1$, $R^2$ for a compound correspond in each case to one row of Table A Table 117
Compounds of the formulae Ia, Ib, Ic, Id, Ie, If, Ig, Ih, Ii and Va in which $L_n$ is 2,6-difluoro-4-methoxycarbonyl, $R^3$ is methoxy and $R^1$, $R^2$ for a compound correspond in each case to one row of Table A Table 118
Compounds of the formulae Ia, Ib, Ic, Id, Ie, If, Ig, Ih, Ii and Va in which $L_n$ is 2-chloro, 4-methoxy, $R^3$ is methoxy and $R^1$, $R^2$ for a compound correspond in each case to one row of Table A Table 119
Compounds of the formulae Ia, Ib, Ic, Id, Ie, If, Ig, Ih, Ii and Va in which $L_n$ is 2-chloro, 4-methyl, $R^3$ is methoxy and $R^1$, $R^2$ for a compound correspond in each case to one row of Table A Table 120
Compounds of the formulae Ia, Ib, Ic, Id, Ie, If, Ig, Ih, Ii and Va in which $L_n$ is 2-chloro, 4-methoxycarbonyl, $R^3$ is methoxy and $R^1$, $R^2$ for a compound correspond in each case to one row of Table A Table 121
Compounds of the formulae Ia, Ib, Ic, Id, Ie, If, Ig, Ih, Ii and Va in which $L_n$ is 2-chloro, 4-methoxy, $R^3$ is methoxy and $R^1$, $R^2$ for a compound correspond in each case to one row of Table A Table 122
Compounds of the formulae Ia, Ib, Ic, Id, Ie, If, Ig, Ih, Ii and Va in which $L_n$ is 2-chloro, 4-cyano, $R^3$ is methoxy and $R^1$, $R^2$ for a compound correspond in each case to one row of Table A Table 123
Compounds of the formulae Ia, Ib, Ic, Id, Ie, If, Ig, Ih, Ii and Va in which $L_n$ is 2,6-difluoro, 4-methoxy, $R^3$ is methoxy and $R^1$, $R^2$ for a compound correspond in each case to one row of Table A Table 124
Compounds of the formulae Ia, Ib, Ic, Id, Ie, If, Ig, Ih, Ii and Va in which $L_n$ is 2-fluoro, 3-methyl, $R^3$ is methoxy and $R^1$, $R^2$ for a compound correspond in each case to one row of Table A Table 125
Compounds of the formulae Ia, Ib, Ic, Id, Ie, If, Ig, Ih, Ii and Va in which $L_n$ is 2,5-dimethyl, $R^3$ is methoxy and $R^1$, $R^2$ for a compound correspond in each case to one row of Table A Table 126
Compounds of the formulae Ia, Ib, Ic, Id, Ie, If, Ig, Ih, Ii and Va in which $L_n$ is 2-methyl, 4-cyano, $R^3$ is methoxy and $R^1$, $R^2$ for a compound correspond in each case to one row of Table A Table 127
Compounds of the formulae Ia, Ib, Ic, Id, Ie, If, Ig, Ih, Ii and Va in which $L_n$ is 2-methyl, 4-bromo, $R^3$ is methoxy and $R^1$, $R^2$ for a compound correspond in each case to one row of Table A Table 128
Compounds of the formulae Ia, Ib, Ic, Id, Ie, If, Ig, Ih, Ii and Va in which $L_n$ is 2-methyl, 5-fluoro, $R^3$ is methoxy and $R^1$, $R^2$ for a compound correspond in each case to one row of Table A Table 129
Compounds of the formulae Ia, Ib, Ic, Id, Ie, If, Ig, Ih, Ii and Va in which $L_n$ is 2-methyl, 4-methoxy, $R^3$ is methoxy and $R^1$, $R^2$ for a compound correspond in each case to one row of Table A Table 130
Compounds of the formulae Ia, Ib, Ic, Id, Ie, If, Ig, Ih, Ii and Va in which $L_n$ is 2-methyl, 4-methoxycarbonyl, $R^3$ is methoxy and $R^1$, $R^2$ for a compound correspond in each case to one row of Table A Table 131
Compounds of the formulae Ia, Ib, Ic, Id, Ie, If, Ig, Ih, Ii and Va in which $L_n$ is 2,5-dimethyl, 4-bromo, $R^3$ is methoxy and $R^1$, $R^2$ for a compound correspond in each case to one row of Table A Table 132
Compounds of the formulae Ia, Ib, Ic, Id, Ie, If, Ig, Ih, Ii and Va in which $L_n$ is 2-fluoro, 4-bromo, $R^3$ is methoxy and $R^1$, $R^2$ for a compound correspond in each case to one row of Table A Table 133
Compounds of the formulae Ia, Ib, Ic, Id, Ie, If, Ig, Ih, Ii and Va in which $L_n$ is 2-fluoro, 4-methoxy, $R^3$ is methoxy and $R^1$, $R^2$ for a compound correspond in each case to one row of Table A Table 134
Compounds of the formulae Ia, Ib, Ic, Id, Ie, If, Ig, Ih, Ii and Va in which $L_n$ is 2-fluoro, 5-methyl, $R^3$ is methoxy and $R^1$, $R^2$ for a compound correspond in each case to one row of Table A Table 135
Compounds of the formulae Ia, Ib, Ic, Id, Ie, If, Ig, Ih, Ii and Va in which $L_n$ is pentafluoro, $R^3$ is methoxy and $R^1$, $R^2$ for a compound correspond in each case to one row of Table A Table 136
Compounds of the formulae Ia, Ib, Ic, Id, Ie, If, Ig, Ih, Ii and Va in which $L_n$ is 2-fluoro, 6-chloro, $R^3$ is cyano and $R^1$, $R^2$ for a compound correspond in each case to one row of Table A Table 137
Compounds of the formulae Ia, Ib, Ic, Id, Ie, If, Ig, Ih, Ii and Va in which $L_n$ is 2,6-difluoro, $R^3$ is cyano and $R^1$, $R^2$ for a compound correspond in each case to one row of Table A Table 138
Compounds of the formulae Ia, Ib, Ic, Id, Ie, If, Ig, Ih, Ii and Va in which $L_n$ is 2,6-dichloro, $R^3$ is cyano and $R^1$, $R^2$ for a compound correspond in each case to one row of Table A Table 139
Compounds of the formulae Ia, Ib, Ic, Id, Ie, If, Ig, Ih, Ii and Va in which $L_n$ is 2-fluoro, 6-methyl, $R^3$ is cyano and $R^1$, $R^2$ for a compound correspond in each case to one row of Table A Table 140
Compounds of the formulae Ia, Ib, Ic, Id, Ie, If, Ig, Ih, Ii and Va in which $L_n$ is 2,4,6-trifluoro, $R^3$ is cyano and $R^1$, $R^2$ for a compound correspond in each case to one row of Table A Table 141
Compounds of the formulae Ia, Ib, Ic, Id, Ie, If, Ig, Ih, Ii and Va in which $L_n$ is 2-methyl, 4-fluoro, $R^3$ is cyano and $R^1$, $R^2$ for a compound correspond in each case to one row of Table A Table 142
Compounds of the formulae Ia, Ib, Ic, Id, Ie, If, Ig, Ih, Ii and Va in which $L_n$ is 2-fluoro, 4-methoxycarbonyl, $R^3$ is cyano and $R^1$, $R^2$ for a compound correspond in each case to one row of Table A Table 143
Compounds of the formulae Ia, Ib, Ic, Id, Ie, If, Ig, Ih, Ii and Va in which $L_n$ is 2-fluoro, 4-CN, $R^3$ is cyano and $R^1$, $R^2$ for a compound correspond in each case to one row of Table A Table 144
Compounds of the formulae Ia, Ib, Ic, Id, Ie, If, Ig, Ih, Ii and Va in which $L_n$ is 2,4,5-trifluoro, $R^3$ is cyano and $R^1$, $R^2$ for a compound correspond in each case to one row of Table A Table 145
Compounds of the formulae Ia, Ib, Ic, Id, Ie, If, Ig, Ih, Ii and Va in which $L_n$ is 2,4-dichloro, $R^3$ is cyano and $R^1$, $R^2$ for a compound correspond in each case to one row of Table A Table 146
Compounds of the formulae Ia, Ib, Ic, Id, Ie, If, Ig, Ih, Ii and Va in which $L_n$ is 2-chloro, $R^3$ is cyano and $R^1$, $R^2$ for a compound correspond in each case to one row of Table A Table 147
Compounds of the formulae Ia, Ib, Ic, Id, Ie, If, Ig, Ih, Ii and Va in which $L_n$ is 2-fluoro, $R^3$ is cyano and $R^1$, $R^2$ for a compound correspond in each case to one row of Table A Table 148
Compounds of the formulae Ia, Ib, Ic, Id, Ie, If, Ig, Ih, Ii and Va in which $L_n$ is 2,4-difluoro, $R^3$ is cyano and $R^1$, $R^2$ for a compound correspond in each case to one row of Table A Table 149
Compounds of the formulae Ia, Ib, Ic, Id, Ie, If, Ig, Ih, Ii and Va in which $L_n$ is 2-fluoro-4-chloro, $R^3$ is cyano and $R^1$, $R^2$ for a compound correspond in each case to one row of Table A Table 150
Compounds of the formulae Ia, Ib, Ic, Id, Ie, If, Ig, Ih, Ii and Va in which $L_n$ is 2-chloro-4-fluoro, $R^3$ is cyano and $R^1$, $R^2$ for a compound correspond in each case to one row of Table A Table 151
Compounds of the formulae Ia, Ib, Ic, Id, Ie, If, Ig, Ih, Ii and Va in which $L_n$ is 2,3-difluoro, $R^3$ is cyano and $R^1$, $R^2$ for a compound correspond in each case to one row of Table A Table 152
Compounds of the formulae Ia, Ib, Ic, Id, Ie, If, Ig, Ih, Ii and Va in which $L_n$ is 2,5-difluoro, $R^3$ is cyano and $R^1$, $R^2$ for a compound correspond in each case to one row of Table A Table 153
Compounds of the formulae Ia, Ib, Ic, Id, Ie, If, Ig, Ih, Ii and Va in which $L_n$ is 2,3,4-trifluoro, $R^3$ is cyano and $R^1$, $R^2$ for a compound correspond in each case to one row of Table A Table 154
Compounds of the formulae Ia, Ib, Ic, Id, Ie, If, Ig, Ih, Ii and Va in which $L_n$ is 2-methyl, $R^3$ is cyano and $R^1$, $R^2$ for a compound correspond in each case to one row of Table A Table 155
Compounds of the formulae Ia, Ib, Ic, Id, Ie, If, Ig, Ih, Ii and Va in which $L_n$ is 2,4-dimethyl, $R^3$ is cyano and $R^1$, $R^2$ for a compound correspond in each case to one row of Table A Table 156
Compounds of the formulae Ia, Ib, Ic, Id, Ie, If, Ig, Ih, Ii and Va in which $L_n$ is 2-methyl-4-chloro, $R^3$ is cyano and $R^1$, $R^2$ for a compound correspond in each case to one row of Table A Table 157
Compounds of the formulae Ia, Ib, Ic, Id, Ie, If, Ig, Ih, Ii and Va in which $L_n$ is 2-fluoro-4-methyl, $R^3$ is cyano and $R^1$, $R^2$ for a compound correspond in each case to one row of Table A Table 158
Compounds of the formulae Ia, Ib, Ic, Id, Ie, If, Ig, Ih, Ii and Va in which $L_n$ is 2,6-dimethyl, $R^3$ is cyano and $R^1$, $R^2$ for a compound correspond in each case to one row of Table A Table 159
Compounds of the formulae Ia, Ib, Ic, Id, Ie, If, Ig, Ih, Ii and Va in which $L_n$ is 2,4,6-trimethyl, $R^3$ is cyano and $R^1$, $R^2$ for a compound correspond in each case to one row of Table A Table 160
Compounds of the formulae Ia, Ib, Ic, Id, Ie, If, Ig, Ih, Ii and Va in which $L_n$ is 2,6-difluoro-4-cyano, $R^3$ is cyano and $R^1$, $R^2$ for a compound correspond in each case to one row of Table A Table 161
Compounds of the formulae Ia, Ib, Ic, Id, Ie, If, Ig, Ih, Ii and Va in which $L_n$ is 2,6-difluoro-4-methyl, $R^3$ is cyano and $R^1$, $R^2$ for a compound correspond in each case to one row of Table A Table 162
Compounds of the formulae Ia, Ib, Ic, Id, Ie, If, Ig, Ih, Ii and Va in which $L_n$ is 2,6-difluoro-4-methoxycarbonyl, $R^3$ is cyano and $R^1$, $R^2$ for a compound correspond in each case to one row of Table A Table 163
Compounds of the formulae Ia, Ib, Ic, Id, Ie, If, Ig, Ih, Ii and Va in which $L_n$ is 2-chloro, 4-methoxy, $R^3$ is cyano and $R^1$, $R^2$ for a compound correspond in each case to one row of Table A Table 164
Compounds of the formulae Ia, Ib, Ic, Id, Ie, If, Ig, Ih, Ii and Va in which $L_n$ is 2-chloro, 4-methyl, $R^3$ is cyano and $R^1$, $R^2$ for a compound correspond in each case to one row of Table A Table 165
Compounds of the formulae Ia, Ib, Ic, Id, Ie, If, Ig, Ih, Ii and Va in which $L_n$ is 2-chloro, 4-methoxycarbonyl, $R^3$ is cyano and $R^1$, $R^2$ for a compound correspond in each case to one row of Table A Table 166
Compounds of the formulae Ia, Ib, Ic, Id, Ie, If, Ig, Ih, Ii and Va in which $L_n$ is 2-chloro, 4-bromo, $R^3$ is cyano and $R^1$, $R^2$ for a compound correspond in each case to one row of Table A Table 167
Compounds of the formulae Ia, Ib, Ic, Id, Ie, If, Ig, Ih, Ii and Va in which $L_n$ is 2-chloro, 4-cyano, $R^3$ is cyano and $R^1$, $R^2$ for a compound correspond in each case to one row of Table A Table 168
Compounds of the formulae Ia, Ib, Ic, Id, Ie, If, Ig, Ih, Ii and Va in which $L_n$ is 2,6-difluoro, 4-methoxy, $R^3$ is cyano and $R^1$, $R^2$ for a compound correspond in each case to one row of Table A Table 169
Compounds of the formulae Ia, Ib, Ic, Id, Ie, If, Ig, Ih, Ii and Va in which $L_n$ is 2-fluoro, 3-methyl, $R^3$ is cyano and $R^1$, $R^2$ for a compound correspond in each case to one row of Table A Table 170
Compounds of the formulae Ia, Ib, Ic, Id, Ie, If, Ig, Ih, Ii and Va in which $L_n$ is 2,5-dimethyl, $R^3$ is cyano and $R^1$, $R^2$ for a compound correspond in each case to one row of Table A Table 171
Compounds of the formulae Ia, Ib, Ic, Id, Ie, If, Ig, Ih, Ii and Va in which $L_n$ is 2-methyl, 4-cyano, $R^3$ is cyano and $R^1$, $R^2$ for a compound correspond in each case to one row of Table A Table 172
Compounds of the formulae Ia, Ib, Ic, Id, Ie, If, Ig, Ih, Ii and Va in which $L_n$ is 2-methyl, 4-bromo, $R^3$ is cyano and $R^1$, $R^2$ for a compound correspond in each case to one row of Table A Table 173
Compounds of the formulae Ia, Ib, Ic, Id, Ie, If, Ig, Ih, Ii and Va in which $L_n$ is 2-methyl, 5-fluoro, $R^3$ is cyano and $R^1$, $R^2$ for a compound correspond in each case to one row of Table A Table 174
Compounds of the formulae Ia, Ib, Ic, Id, Ie, If, Ig, Ih, Ii and Va in which $L_n$ is 2-methyl, 4-methoxy, $R^3$ is cyano and $R^1$, $R^2$ for a compound correspond in each case to one row of Table A Table 175
Compounds of the formulae Ia, Ib, Ic, Id, Ie, If, Ig, Ih, Ii and Va in which $L_n$ is 2-methyl, 4-methoxycarbonyl, $R^3$ is cyano and $R^1$, $R^2$ for a compound correspond in each case to one row of Table A Table 176
Compounds of the formulae Ia, Ib, Ic, Id, Ie, If, Ig, Ih, Ii and Va in which $L_n$ is 2,5-dimethyl, 4-bromo, $R^3$ is cyano and $R^1$, $R^2$ for a compound correspond in each case to one row of Table A Table 177
Compounds of the formulae Ia, Ib, Ic, Id, Ie, If, Ig, Ih, Ii and Va in which $L_n$ is 2-fluoro, 4-bromo, $R^3$ is cyano and $R^1$, $R^2$ for a compound correspond in each case to one row of Table A Table 178
Compounds of the formulae Ia, Ib, Ic, Id, Ie, If, Ig, Ih, Ii and Va in which $L_n$ is 2-fluoro, 4-methoxy, $R^3$ is cyano and $R^1$, $R^2$ for a compound correspond in each case to one row of Table A Table 179
Compounds of the formulae Ia, Ib, Ic, Id, Ie, If, Ig, Ih, Ii and Va in which $L_n$ is 2-fluoro, 5-methyl, $R^3$ is cyano and $R^1$, $R^2$ for a compound correspond in each case to one row of Table A Table 180
Compounds of the formulae Ia, Ib, Ic, Id, Ie, If, Ig, Ih, Ii and Va in which $L_n$ is pentafluoro, $R^3$ is cyano and $R^1$, $R^2$ for a compound correspond in each case to one row of Table A

TABLE A

| No. | $R^1$ | $R^2$ |
|---|---|---|
| A-1 | $CH_2CH_3$ | H |
| A-2 | $CH_2CH_3$ | $CH_3$ |
| A-3 | $CH_2CH_3$ | $CH_2CH_3$ |
| A-4 | $CH_2CH_2CH_3$ | H |
| A-5 | $CH_2CH_2CH_3$ | $CH_3$ |
| A-6 | $CH_2CH_2CH_3$ | $CH_2CH_3$ |
| A-7 | $CH_2CH_2CH_3$ | $CH_2CH_2CH_3$ |
| A-8 | $CH_2CH_2F$ | H |
| A-9 | $CH_2CH_2F$ | $CH_3$ |
| A-10 | $CH_2CH_2F$ | $CH_2CH_3$ |
| A-11 | $CH_2CF_3$ | H |
| A-12 | $CH_2CF_3$ | $CH_3$ |
| A-13 | $CH_2CF_3$ | $CH_2CH_3$ |
| A-14 | $CH_2CF_3$ | $CH_2CH_2CH_3$ |
| A-15 | $CH_2CCl_3$ | H |
| A-16 | $CH_2CCl_3$ | $CH_3$ |
| A-17 | $CH_2CCl_3$ | $CH_2CH_3$ |
| A-18 | $CH_2CCl_3$ | $CH_2CH_2CH_3$ |
| A-19 | $CH(CH_3)_2$ | H |
| A-20 | $CH(CH_3)_2$ | $CH_3$ |
| A-21 | $CH(CH_3)_2$ | $CH_2CH_3$ |
| A-22 | $CH(CH_3)_2$ | $CH_2CH_2CH_3$ |
| A-23 | $CH_2C(CH_3)_3$ | H |

TABLE A-continued

| No. | R¹ | R² |
|---|---|---|
| A-24 | CH₂C(CH₃)₃ | CH₃ |
| A-25 | CH₂C(CH₃)₃ | CH₂CH₃ |
| A-26 | CH₂CH(CH₃)₂ | H |
| A-27 | CH₂CH(CH₃)₂ | CH₃ |
| A-28 | CH₂CH(CH₃)₂ | CH₂CH₃ |
| A-29 | (±) CH(CH₂CH₃)CH₃ | H |
| A-30 | (±) CH(CH₂CH₃)CH₃ | CH₃ |
| A-31 | (±) CH(CH₂CH₃)CH₃ | CH₂CH₃ |
| A-32 | (R) CH(CH₂CH₃)CH₃ | H |
| A-33 | (R) CH(CH₂CH₃)CH₃ | CH₃ |
| A-34 | (R) CH(CH₂CH₃)CH₃ | CH₂CH₃ |
| A-35 | (S) CH(CH₂CH₃)CH₃ | H |
| A-36 | (S) CH(CH₂CH₃)CH₃ | CH₃ |
| A-37 | (S) CH(CH₂CH₃)CH₃ | CH₂CH₃ |
| A-38 | (±) CH(CH₃)—CH(CH₃)₂ | H |
| A-39 | (±) CH(CH₃)—CH(CH₃)₂ | CH₃ |
| A-40 | (±) CH(CH₃)—CH(CH₃)₂ | CH₂CH₃ |
| A-41 | (R) CH(CH₃)—CH(CH₃)₂ | H |
| A-42 | (R) CH(CH₃)—CH(CH₃)₂ | CH₃ |
| A-43 | (R) CH(CH₃)—CH(CH₃)₂ | CH₂CH₃ |
| A-44 | (S) CH(CH₃)—CH(CH₃)₂ | H |
| A-45 | (S) CH(CH₃)—CH(CH₃)₂ | CH₃ |
| A-46 | (S) CH(CH₃)—CH(CH₃)₂ | CH₂CH₃ |
| A-47 | (±) CH(CH₃)—C(CH₃)₃ | H |
| A-48 | (±) CH(CH₃)—C(CH₃)₃ | CH₃ |
| A-49 | (±) CH(CH₃)—C(CH₃)₃ | CH₂CH₃ |
| A-50 | (R) CH(CH₃)—C(CH₃)₃ | H |
| A-51 | (R) CH(CH₃)—C(CH₃)₃ | CH₃ |
| A-52 | (R) CH(CH₃)—C(CH₃)₃ | CH₂CH₃ |
| A-53 | (S) CH(CH₃)—C(CH₃)₃ | H |
| A-54 | (S) CH(CH₃)—C(CH₃)₃ | CH₃ |
| A-55 | (S) CH(CH₃)—C(CH₃)₃ | CH₂CH₃ |
| A-56 | (±) CH(CH₃)—CF₃ | H |
| A-57 | (±) CH(CH₃)—CF₃ | CH₃ |
| A-58 | (±) CH(CH₃)—CF₃ | CH₂CH₃ |
| A-59 | (R) CH(CH₃)—CF₃ | H |
| A-60 | (R) CH(CH₃)—CF₃ | CH₃ |
| A-61 | (R) CH(CH₃)—CF₃ | CH₂CH₃ |
| A-62 | (S) CH(CH₃)—CF₃ | H |
| A-63 | (S) CH(CH₃)—CF₃ | CH₃ |
| A-64 | (S) CH(CH₃)—CF₃ | CH₂CH₃ |
| A-65 | (±) CH(CH₃)—CCl₃ | H |
| A-66 | (±) CH(CH₃)—CCl₃ | CH₃ |
| A-67 | (±) CH(CH₃)—CCl₃ | CH₂CH₃ |
| A-68 | (R) CH(CH₃)—CCl₃ | H |
| A-69 | (R) CH(CH₃)—CCl₃ | CH₃ |
| A-70 | (R) CH(CH₃)—CCl₃ | CH₂CH₃ |
| A-71 | (S) CH(CH₃)—CCl₃ | H |
| A-72 | (S) CH(CH₃)—CCl₃ | CH₃ |
| A-73 | (S) CH(CH₃)—CCl₃ | CH₂CH₃ |
| A-74 | CH₂C(CH₃)=CH₂ | H |
| A-75 | CH₂C(CH₃)=CH₂ | CH₃ |
| A-76 | CH₂C(CH₃)=CH₂ | CH₂CH₃ |
| A-77 | cyclopentyl | H |
| A-78 | cyclopentyl | CH₃ |
| A-79 | cyclopentyl | CH₂CH₃ |
| A-80 | cyclohexyl | H |
| A-81 | cyclohexyl | CH₃ |
| A-82 | cyclohexyl | CH₂CH₃ |
| A-83 | —(CH₂)₄— | |
| A-84 | (±) —(CH₂)₂—CH(CH₃)—CH₂— | |
| A-85 | (R) —(CH₂)₂—CH(CH₃)—CH₂— | |
| A-86 | (S) —(CH₂)₂—CH(CH₃)—CH₂— | |
| A-87 | —(CH₂)₂—CH(OCH₃)—CH₂— | |
| A-88 | —(CH₂)₂—CH(CH₂CH₃)—CH₂— | |
| A-89 | —(CH₂)₂—CH[CH(CH₃)₂]—CH₂— | |
| A-90 | (±) —(CH₂)₃—CH(CH₃)— | |
| A-91 | (±) —CH(CH₃)—(CH₂)₂—CH(CH₃)— | |
| A-92 | —CH₂—CH=CH—CH₂— | |
| A-93 | —(CH₂)₅— | |
| A-94 | (±) —(CH₂)₄—CH(CH₃)— | |
| A-95 | —(CH₂)₂—CH(CH₃)—(CH₂)₂— | |
| A-96 | (±) —(CH₂)₃—CH(CH₃)—CH₂— | |
| A-97 | (R) —(CH₂)₃—CH(CH₃)—CH₂— | |
| A-98 | (S) —(CH₂)₃—CH(CH₃)—CH₂— | |
| A-99 | —(CH₂)₂—C(O[CH₂]₂O)—(CH₂)₂— | |

TABLE A-continued

| No. | R¹ | R² |
|---|---|---|
| A-100 | (CH₂)₂—△—CH₂ | |
| A-101 | —(CH₂)₂—C(O[CH₂]₃O)—(CH₂)₂— | |
| A-102 | —(CH₂)₂—CH=CH—CH₂— | |

Furthermore with a view to their use, preference is given to the compounds I compiled in the tables below. Moreover, the groups mentioned for a substituent in the tables are per se, independently of the combination in which they are mentioned, a particularly preferred embodiment of the substituent in question.

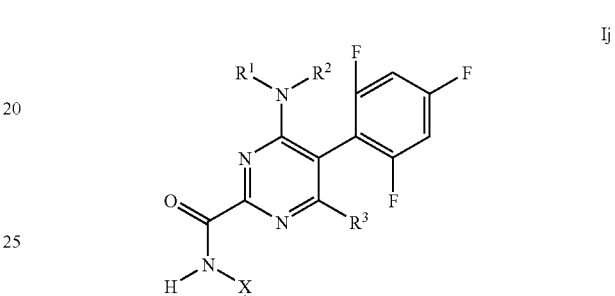

Ij

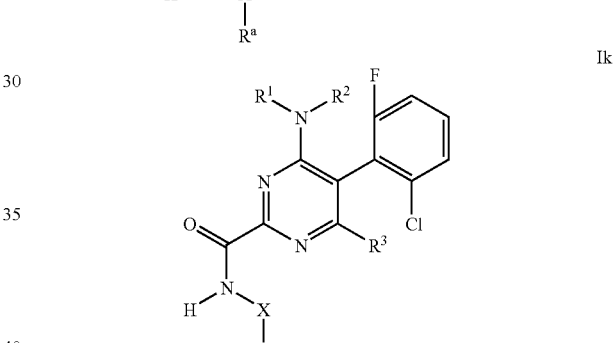

Ik

Table 181
Compounds of the formulae Ij and Ik in which NR¹R² is 4-methylpiperidine and R³ is methyl and —X—Rᵃ for a compound corresponds in each case to one row of Table B Table 182
Compounds of the formulae Ij and Ik in which R¹ is CH(CH₃)₂, R² is hydrogen and R³ is methyl and —X—Rᵃ for a compound corresponds in each case to one row of Table B Table 183
Compounds of the formulae Ij and Ik in which R¹ is CH₂CF₃, R² is hydrogen and R³ is methyl and —X—Rᵃ for a compound corresponds in each case to one row of Table B Table 184
Compounds of the formulae Ij and Ik in which R¹ is (R,S)CH(CH₃)CH₂CH₃, R² is hydrogen and R³ is methyl and —X—Rᵃ for a compound corresponds in each case to one row of Table B Table 185
Compounds of the formulae Ij and Ik in which R¹ is (R)CH(CH₃)CH₂CH₃, R² is hydrogen and R³ is methyl and —X—Rᵃ for a compound corresponds in each case to one row of Table B Table 186
Compounds of the formulae Ij and Ik in which $R^1$ is (S)CH(CH$_3$)CH$_2$CH$_3$, $R^2$ is hydrogen and $R^3$ is methyl and —X—$R^a$ for a compound corresponds in each case to one row of Table B Table 187
Compounds of the formulae Ij and Ik in which $R^1$ is (R,S)CH(CH$_3$)CF$_3$, $R^2$ is hydrogen and $R^3$ is methyl and —X—$R^a$ for a compound corresponds in each case to one row of Table B Table 188
Compounds of the formulae Ij and Ik in which $R^1$ is (R)CH(CH$_3$)CF$_3$, $R^2$ is hydrogen and $R^3$ is methyl and —X—$R^a$ for a compound corresponds in each case to one row of Table B Table 189
Compounds of the formulae Ij and Ik in which $R^1$ is (S)CH(CH$_3$)CF$_3$, $R^2$ is hydrogen and $R^3$ is methyl and —X—$R^a$ for a compound corresponds in each case to one row of Table B Table 190
Compounds of the formulae Ij and Ik in which NR$^1$R$^2$ is 4-methylpiperidine and $R^3$ is chloro and —X—$R^a$ for a compound corresponds in each case to one row of Table B Table 191
Compounds of the formulae Ij and Ik in which $R^1$ is CH(CH$_3$)$_2$, $R^2$ is hydrogen and $R^3$ is chloro and —X—$R^a$ for a compound corresponds in each case to one row of Table B Table 192
Compounds of the formulae Ij and Ik in which $R^1$ is CH$_2$CF$_3$, $R^2$ is hydrogen and $R^3$ is chloro and —X—$R^a$ for a compound corresponds in each case to one row of Table B Table 193
Compounds of the formulae Ij and Ik in which $R^1$ is (R,S)CH(CH$_3$)CH$_2$CH$_3$, $R^2$ is hydrogen and $R^3$ is chloro and —X—$R^a$ for a compound corresponds in each case to one row of Table B Table 194
Compounds of the formulae Ij and Ik in which $R^1$ is (R)CH(CH$_3$)CH$_2$CH$_3$, $R^2$ is hydrogen and $R^3$ is chloro and —X—$R^a$ for a compound corresponds in each case to one row of Table B Table 195
Compounds of the formulae Ij and Ik in which $R^1$ is (S)CH(CH$_3$)CH$_2$CH$_3$, $R^2$ is hydrogen and $R^3$ is chloro and —X—$R^a$ for a compound corresponds in each case to one row of Table B Table 196
Compounds of the formulae Ij and Ik in which $R^1$ is (R,S)CH(CH$_3$)CF$_3$, $R^2$ is hydrogen and $R^3$ is chloro and —X—$R^a$ for a compound corresponds in each case to one row of Table B Table 197
Compounds of the formulae Ij and Ik in which $R^1$ is (R)CH(CH$_3$)CF$_3$, $R^2$ is hydrogen and $R^3$ is chloro and —X—$R^a$ for a compound corresponds in each case to one row of Table B Table 198
Compounds of the formulae Ij and Ik in which $R^1$ is (S)CH(CH$_3$)CF$_3$, $R^2$ is hydrogen and $R^3$ is chloro and —X—$R^a$ for a compound corresponds in each case to one row of Table B Table 199
Compounds of the formulae Ij and Ik in which NR$^1$R$^2$ is 4-methylpiperidine and $R^3$ is methoxy and —X—$R^a$ for a compound corresponds in each case to one row of Table B Table 200
Compounds of the formulae Ij and Ik in which $R^1$ is CH(CH$_3$)$_2$, $R^2$ is hydrogen and $R^3$ is methoxy and —X—$R^a$ for a compound corresponds in each case to one row of Table B Table 201
Compounds of the formulae Ij and Ik in which $R^1$ is CH$_2$CF$_3$, $R^2$ is hydrogen and $R^3$ is methoxy and —X—$R^a$ for a compound corresponds in each case to one row of Table B Table 202
Compounds of the formulae Ij and Ik in which $R^1$ is (R,S)CH(CH$_3$)CH$_2$CH$_3$, $R^2$ is hydrogen and $R^3$ is methoxy and —X—$R^a$ for a compound corresponds in each case to one row of Table B Table 203
Compounds of the formulae Ij and Ik in which $R^1$ is (R)CH(CH$_3$)CH$_2$CH$_3$, $R^2$ is hydrogen and $R^3$ is methoxy and —X—$R^a$ for a compound corresponds in each case to one row of Table B Table 204
Compounds of the formulae Ij and Ik in which $R^1$ is (S)CH(CH$_3$)CH$_2$CH$_3$, $R^2$ is hydrogen and $R^3$ is methoxy and —X—$R^a$ for a compound corresponds in each case to one row of Table B Table 205
Compounds of the formulae Ij and Ik in which $R^1$ is (R,S)CH(CH$_3$)CF$_3$, $R^2$ is hydrogen and $R^3$ is methoxy and —X—$R^a$ for a compound corresponds in each case to one row of Table B Table 206
Compounds of the formulae Ij and Ik in which $R^1$ is (R)CH(CH$_3$)CF$_3$, $R^2$ is hydrogen and $R^3$ is methoxy and —X—$R^a$ for a compound corresponds in each case to one row of Table B Table 207
Compounds of the formulae Ij and Ik in which $R^1$ is (S)CH(CH$_3$)CF$_3$, $R^2$ is hydrogen and $R^3$ is methoxy and —X—$R^a$ for a compound corresponds in each case to one row of Table B Table 208
Compounds of the formulae Ij and Ik in which NR$^1$R$^2$ is 4-methylpiperidine and $R^3$ is cyano and —X—$R^a$ for a compound corresponds in each case to one row of Table B Table 209
Compounds of the formulae Ij and Ik in which $R^1$ is CH(CH$_3$)$_2$, $R^2$ is hydrogen and $R^3$ is cyano and —X—$R^a$ for a compound corresponds in each case to one row of Table B Table 210
Compounds of the formulae Ij and Ik in which $R^1$ is CH$_2$CF$_3$, $R^2$ is hydrogen and $R^3$ is cyano and —X—$R^a$ for a compound corresponds in each case to one row of Table B Table 211

Compounds of the formulae Ij and Ik in which $R^1$ is $(R,S)CH(CH_3)CH_2CH_3$, $R^2$ is hydrogen and $R^3$ is cyano and —X—$R^a$ for a compound corresponds in each case to one row of Table B Table 212

Compounds of the formulae Ij and Ik in which $R^1$ is $(R)CH(CH_3)CH_2CH_3$, $R^2$ is hydrogen and $R^3$ is cyano and —X—$R^a$ for a compound corresponds in each case to one row of Table B Table 213

Compounds of the formulae Ij and Ik in which $R^1$ is $(S)CH(CH_3)CH_2CH_3$, $R^2$ is hydrogen and $R^3$ is cyano and —X—$R^a$ for a compound corresponds in each case to one row of Table B Table 214

Compounds of the formulae Ij and Ik in which $R^1$ is $(R,S)CH(CH_3)CF_3$, $R^2$ is hydrogen and $R^3$ is cyano and —X—$R^a$ for a compound corresponds in each case to one row of Table B Table 215

Compounds of the formulae Ij and Ik in which $R^1$ is $(R)CH(CH_3)CF_3$, $R^2$ is hydrogen and $R^3$ is cyano and —X—$R^a$ for a compound corresponds in each case to one row of Table B Table 216

Compounds of the formulae Ij and Ik in which $R^1$ is $(S)CH(CH_3)CF_3$, $R^2$ is hydrogen and $R^3$ is cyano and —X—$R^a$ for a compound corresponds in each case to one row of Table B

TABLE B

| No. | X | $R^a$ |
|---|---|---|
| B-1 | —(C=O)— | H |
| B-2 | | $CH_3$ |
| B-3 | | $CH_2CH_3$ |
| B-4 | | $CH_2CH_2CH_3$ |
| B-5 | | $CH_2CH(CH_3)_2$ |
| B-6 | | $CH_2C(CH_3)_3$ |
| B-7 | —O— | H |
| B-8 | | $CH_3$ |
| B-9 | | $CH_2CH_3$ |
| B-10 | | $CH_2CH_2CH_3$ |
| B-11 | | $CH_2CH(CH_3)_2$ |
| B-12 | | $CH_2C(CH_3)_3$ |
| B-13 | —(C=O)—O— | H |
| B-14 | | $CH_3$ |
| B-15 | | $CH_2CH_3$ |
| B-16 | | $CH_2CH_2CH_3$ |
| B-17 | | $CH_2CH(CH_3)_2$ |
| B-18 | | $CH_2C(CH_3)_3$ |
| B-19 | —NH— | H |
| B-20 | | $CH_3$ |
| B-21 | | $CH_2CH_3$ |
| B-22 | | $CH_2CH_2CH_3$ |
| B-23 | | $CH_2CH(CH_3)_2$ |
| B-24 | | $CH_2C(CH_3)_3$ |
| B-25 | —(C=O)—NH— | H |
| B-26 | | $CH_3$ |
| B-27 | | $CH_2CH_3$ |
| B-28 | | $CH_2CH_2CH_3$ |
| B-29 | | $CH_2CH(CH_3)_2$ |
| B-30 | | $CH_2C(CH_3)_3$ |
| B-31 | direct bond | H |
| B-32 | | $CH_3$ |
| B-33 | | $CH_2CH_3$ |
| B-34 | | $CH_2CH_2CH_3$ |
| B-35 | | $CH_2CH(CH_3)_2$ |
| B-36 | | $CH_2C(CH_3)_3$ |

TABLE B-continued

| No. | X | $R^a$ |
|---|---|---|
| B-37 | | $CH_2OH$ |
| B-38 | | $CH_2CH_2OH$ |
| B-39 | | $CH_2CH_2CH_2OH$ |
| B-40 | | $CH_2CH_2CH_2CH_2OH$ |
| B-41 | | $CH_2OCH_3$ |
| B-42 | | $CH_2CH_2OCH3$ |
| B-43 | | $CH_2CH_2CH_2OCH_3$ |
| B-44 | | $CH_2CH_2CH_2CH_2OCH_3$ |
| B-45 | | $CH_2OCH_2CH_3$ |
| B-46 | | $CH_2CH_2OCH_2CH_3$ |
| B-47 | | $CH_2CH_2CH_2OCH_2CH_3$ |
| B-48 | | $CH_2NH_2$ |
| B-49 | | $CH_2CH_2NH_2$ |
| B-50 | | $CH_2CH_2CH_2NH_2$ |
| B-51 | | $CH_2NHCH_3$ |
| B-52 | | $CH_2CH_2NHCH_3$ |
| B-53 | | $CH_2CH_2CH_2NHCH_3$ |
| B-54 | | $CH_2NHCH_2CH_3$ |
| B-55 | | $CH_2CH_2NHCH_2CH_3$ |
| B-56 | | $CH_2CH_2CH_2NHCH_2CH_3$ |
| B-57 | | $CH_2N(CH_3)_2$ |
| B-58 | | $CH_2SH$ |
| B-59 | | $CH_2CH_2SH$ |
| B-60 | | $CH_2CH_2CH_2SH$ |
| B-61 | | $CH_2SCH_3$ |
| B-62 | | $CH_2CH_2SCH_3$ |
| B-63 | | $CH_2CH_2CH_2SCH_3$ |
| B-64 | | $CH_2SCH_2CH_3$ |
| B-65 | | $CH_2CH_2SCH_2CH_3$ |
| B-66 | | $CH_2CH_2CH_2SCH_2CH_3$ |
| B-67 | | $CH(OCH_3)_2$ |
| B-68 | | $CH_2CH(OCH_3)_2$ |
| B-69 | | $CH_2CH_2CH(OCH_3)_2$ |
| B-70 | | 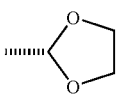 |
| B-71 | | 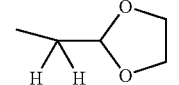 |
| B-72 | | 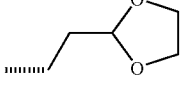 |
| B-73 | | 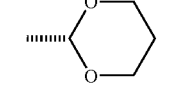 |
| B-74 | | 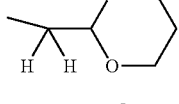 |
| B-75 | | 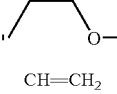 |
| B-76 | | $CH=CH_2$ |
| B-77 | | $CH=CH_2CH_3$ |
| B-78 | | $CH_2CH=CH_2$ |
| B-79 | | $CH_2CH_2CH=CH_2$ |
| B-80 | | $CH_2C≡CH$ |
| B-81 | | $CH_2CH_2C≡CH$ |

The compounds I are suitable as fungicides. They are distinguished by an outstanding effectiveness against a broad spectrum of phytopathogenic fungi, especially from the classes of the Ascomycetes, Deuteromycetes, Oomycetes and Basidiomycetes. Some are systemically effective and they can be used in plant protection as foliar and soil fungicides.

They are particularly important in the control of a multitude of fungi on various cultivated plants, such as wheat, rye, barley, oats, rice, corn, grass, bananas, cotton, soybean, coffee, sugar cane, vines, fruits and ornamental plants, and vegetables, such as cucumbers, beans, tomatoes, potatoes and cucurbits, and on the seeds of these plants.

They are especially suitable for controlling the following plant diseases:

*Alternaria* species on fruit and vegetables,
*Bipolaris* and *Drechslera* species on cereals, rice and lawns,
*Blumeria graminis* (powdery mildew) on cereals,
*Botrytis cinerea* (gray mold) on strawberries, vegetables, ornamental plants and grapevines,
*Erysiphe cichoracearum* and *Sphaerotheca fuliginea* on cucurbits,
*Fusarium* and *Verticillium* species on various plants,
*Mycosphaerella* species on cereals, bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
*Pseudoperonospora* species on hops and cucumbers,
*Puccinia* species on cereals,
*Pyricularia oryzae* on rice,
*Rhizoctonia* species on cotton, rice and lawns,
*Septoria tritici* and *Stagonospora nodorum* on wheat,
*Uncinula necator* on grapevines,
*Ustilago* species on cereals and sugar cane, and
*Venturia* species (scab) on apples and pears.

The compounds I are also suitable for controlling harmful fungi, such as *Paecilomyces variotii*, in the protection of materials (for example wood, paper, paint dispersions, fibers or fabrics) and in the protection of stored products.

The compounds I are employed by treating the fungi or the plants, seeds, materials or soil to be protected against fungal attack with a fungicidally effective amount of the active compounds. The application can be carried out both before and after the infection of the materials, plants or seeds by the fungi.

The fungicidal compositions generally comprise between 0.1 and 95%, preferably between 0.5 and 90%, by weight of active compound.

When employed in plant protection, the amounts applied are, depending on the kind of effect desired, between 0.01 and 2.0 kg of active compound per ha.

In seed treatment, amounts of active compound of 0.001 to 0.1 g, preferably 0.01 to 0.05 g, per kilogram of seed are generally necessary.

When used in the protection of materials or stored products, the amount of active compound applied depends on the kind of application area and on the desired effect. Amounts customarily applied in the protection of materials are, for example, 0.001 g to 2 kg, preferably 0.005 g to 1 kg, of active compound per cubic meter of treated material.

The compounds I can be converted to the customary formulations, for example solutions, emulsions, suspensions, dusts, powders, pastes and granules. The application form depends on the particular intended use; it should in each case ensure a fine and uniform distribution of the compound according to the invention.

The formulations are prepared in a known manner, for example by extending the active compound with solvents and/or carriers, if desired using emulsifiers and dispersants. Solvents/auxiliaries which are suitable are essentially:

water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

carriers such as ground natural minerals (for example kaolins, clays, talc, chalk) and ground synthetic minerals (for example highly disperse silica, silicates); emulsifiers such as nonionic and anionic emulsifiers (for example polyoxyethylene fatty alcohol ethers, alkylsulfonates and arylsulfonates) and dispersants such as lignosulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound. The active compounds are employed in a purity of from 90% to 100%, preferably 95% to 100% (according to NMR spectrum).

The following are examples of formulations:

1. Products for Dilution with Water

A) Water-Soluble Concentrates (SL)

10 parts by weight of a compound according to the invention are dissolved in water or in a water-soluble solvent. As an alternative, wetters or other auxiliaries are added. The active compound dissolves upon dilution with water.

B) Dispersible Concentrates (DC)

20 parts by weight of a compound according to the invention are dissolved in cyclohexanone with addition of a dispersant, for example polyvinylpyrrolidone. Dilution with water gives a dispersion.

C) Emulsifiable Concentrates (EC)

15 parts by weight of a compound according to the invention are dissolved in xylene with addition of calcium dodecylbenzenesulfonate and castor oil ethoxylate (in each case 5% strength). Dilution with water gives an emulsion.

D) Emulsions (EW, EO)

40 parts by weight of a compound according to the invention are dissolved in xylene with addition of calcium dodecylbenzenesulfonate and castor oil ethoxylate (in each case 5% strength). This mixture is introduced into water by means of an emulsifier (Ultraturvax) and made into a homogeneous emulsion. Dilution with water gives an emulsion.

E) Suspensions (SC, OD)

In an agitated ball mill, 20 parts by weight of a compound according to the invention are comminuted with addition of dispersants, wetters and water or an organic solvent to give a fine active compound suspension. Dilution with water gives a stable suspension of the active compound.

F) Water-Dispersible Granules and Water-Soluble Granules (WG, SG)

50 parts by weight of a compound according to the invention are ground finely with addition of dispersants and wetters and made into water-dispersible or water-soluble granules by means of technical appliances (for example extrusion, spray tower, fluidized bed). Dilution with water gives a stable dispersion or solution of the active compound.

G) Water-Dispersible Powders and Water-Soluble Powders (WP, SP)

75 parts by weight of a compound according to the invention are ground in a rotor-stator mill with addition of dispersants, wetters and silica gel. Dilution with water gives a stable dispersion or solution of the active compound.

2. Products to be Applied Undiluted

H) Dusts (DP)

5 parts by weight of a compound according to the invention are ground finely and mixed intimately with 95% of finely divided kaolin. This gives a dustable product.

I) Granules (GR, FG, GG, MG)

0.5 part by weight of a compound according to the invention is ground finely and associated with 95.5% carriers. Customary methods are extrusion, spray-drying or the fluidized bed. This gives granules to be applied undiluted.

J) ULV Solutions (UL)

10 parts by weight of a compound according to the invention are dissolved in an organic solvent, for example xylene. This gives a product to be applied undiluted.

The active compounds can be used as such, in the form of their formulations or of the application forms prepared therefrom, e.g. in the form of directly sprayable solutions, powders, suspensions or dispersions, emulsions, oil dispersions, pastes, dustable products, preparations for broadcasting or granules, by spraying, atomizing, dusting, broadcasting or watering. The application forms depend entirely on the intended uses; they should always ensure the finest possible dispersion of the active compounds according to the invention.

Aqueous application forms can be prepared from emulsifiable concentrates, pastes or wettable powders (spray powders, oil dispersions) by addition of water. To prepare emulsions, pastes or oil dispersions, the substances can be homogenized in water, as such or dissolved in an oil or solvent, by means of wetting agents, tackifiers, dispersants or emulsifiers. However, it is also possible to prepare concentrates comprising active substance, wetting agent, tackifier, dispersant or emulsifier and possibly solvent or oil which are suitable for dilution with water.

The concentrations of active compound in the ready-for-use preparations can be varied within relatively wide ranges. In general, they are between 0.0001 and 10%, preferably between 0.01 and 1%.

The active compounds can also be used with great success in the ultra-low volume (ULV) process, it being possible to apply formulations with more than 95% by weight of active compound or even the active compound without additives.

Oils of various types, wetting agents, adjuvants, herbicides, fungicides, other pesticides and bactericides can be added to the active compounds, if need be also not until immediately before use (tank mix). These agents can be added to the preparations according to the invention in a weight ratio of 1:10 to 10:1.

The preparations according to the invention can, in the application form as fungicides, also be present together with other active compounds, e.g. with herbicides, insecticides, growth regulators, fungicides or also with fertilizers. On mixing the compounds I or the preparations comprising them in the application form as fungicides with other fungicides, in many cases an expansion of the fungicidal spectrum of activity is obtained.

The following list of fungicides, with which the compounds according to the invention can be used in conjunction, is intended to illustrate the possible combinations but does not limit them:

acylalanines, such as benalaxyl, metalaxyl, ofurace or oxadixyl, amine derivatives, such as aldimorph, dodine, dodemorph, fenpropimorph, fenpropidin, guazatine, iminoctadine, spiroxamine or tridemorph, anilinopyrimidines, such as pyrimethanil, mepanipyrim or cyprodinyl, antibiotics, such as cycloheximide, griseofulvin, kasugamycin, natamycin, polyoxin or streptomycin, azoles, such as bitertanol, bromoconazole, cyproconazole, difenoconazole, dinitroconazole, epoxiconazole, fenbuconazole, fluquinconazole, flusilazole, flutriafol, hexaconazole, imazalil, metconazole, myclobutanil, penconazole, propiconazole, prochloraz, prothioconazole, tebuconazole, triadimefon, triadimenol, triflumizole or triticonazole, dicarboximides, such as iprodione, myclozolin, procymidone or vinclozolin, dithiocarbamates, such as ferbam, nabam, maneb, mancozeb, metam, metiram, propineb, polycarbamate, thiram, ziram or zineb, heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, tiadinil, tricyclazole or triforine, copper fungicides, such as Bordeaux mixture, copper acetate, copper oxychloride or basic copper sulfate, nitrophenyl derivatives, such as binapacryl, dinocap, dinobuton or nitrophthal-isopropyl, phenylpyrroles, such as fenpiclonil or fludioxonil, sulfur, other fungicides, such as acibenzolar-S-methyl, benthiavalicarb, carpropamid, chlorothalonil, cyflufenamid, cymoxanil, dazomet, diclomezine, diclocymet, diethofencarb, edifenphos, ethaboxam, fenhexamid, fentin acetate, fenoxanil, ferimzone, fluazinam, fosetyl, fosetyl-aluminum, iprovalicarb, hexachlorobenzene, metrafenone, pencycuron, propamocarb, phthalide, tolclofos-methyl, quintozene or zoxamide, strobilurins, such as azoxystrobin, dimoxystrobin, fluoxastrobin, kresoxim-methyl, metominostrobin, orysastrobin, picoxystrobin, pyraclostrobin or trifloxystrobin, sulfenic acid derivatives, such as captafol, captan, dichlofluanid, folpet or tolylfluanid, cinnamides and analogous compounds, such as dimethomorph, flumetover or flumorph.

SYNTHESIS EXAMPLES

Example 1

Preparation of 4-chloro-6-((S)-2,2,2-trifluoro-1-methylethylamino)-5-(2,4,6-trifluorophenyl)-pyrimidine-2-carboxamide [I-5]

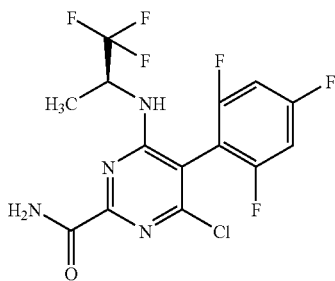

5.0 g of 4-chloro-6-((S)-2,2,2-trifluoro-1-methylethylamino)-5-(2,4,6-trifluorophenyl)-pyrimidine-2-carbonitrile (see WO 03/04993, pages 28 and 29) were initially charged in 5 ml of DMSO, 344 mg of $K_2CO_3$ were added and the mixture was cooled to 10° C. 1.4 ml of 30% strength $H_2O_2$ were then added. The mixture was stirred in an ice bath for 5 min and then at room temperature for another 30 min. The reaction mixture was introduced into 150 ml of water. During the addition, the amide precipitated out. The amide was filtered off, washed and dried under high vacuum. This gave 4.7 g of the beige title compound of m.p. 157-162° C.

Example 2

Preparation of 4-chloro-6-((S)-2,2,2-trifluoro-1-methylethylamino)-5-(2,4,6-trifluorophenyl)-pyrimidine-2-carboxylic acid [I-11]

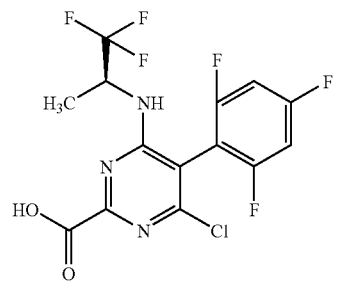

1.5 g of 4-chloro-6-((S)-2,2,2-trifluoro-1-methylethylamino)-5-(2,4,6-trifluorophenyl)-pyrimidine-2-carbonitrile (see WO 03/04993, pages 28 and 29) were dissolved in 5 ml of conc. $H_2SO_4$, and the mixture was stirred at 110° C. for 20 min. The reaction mixture was introduced into 100 ml of ice-water, and during the addition the acid precipitated out. The acid was filtered off, washed with water and dried under high vacuum. This gave 1.5 g of the yellow title compound.

$^1$H-NMR (CDCl$_3$, ppm): 1.4 (d, CH$_3$), 4.85 (d, NH), 5.60-5.80 (m, CH), 6.90-7.00 (m, CH), 10.5 (s (broad), OH).

Example 3

Preparation of N-tert.-butyl-4-chloro-6-((S)-2,2,2-trifluoro-1-methyl-ethylamino)-5-(2,4,6-trifluorophenyl)pyrimidine-2-carboxamide [I-10]

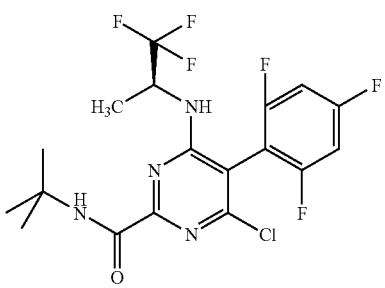

a) 1.5 g of the acid (Example 2) were added to 5 ml of thionyl chloride at 40° C. The reaction mixture was stirred until the evolution of gas had ceased. Toluene was added to the mixture and the solvent and excess thionyl chloride were distilled off completely. This gave 1.6 g of a dark-green oil.

b) 38 mg of tert-butylamine and 58 mg of triethylamine were initially charged in 7 ml of THF at 0° C., and 200 mg of the acid chloride prepared beforehand, dissolved in 2 ml of THF, were added. The reaction mixture was stirred at room temperature for 12 h. The reaction mixture was concentrated using a rotary evaporator, taken up in methyl tert-butyl ether and washed with water. The organic phase was removed, dried over MgSO₄ and concentrated. The crude product was purified by preparative HPLC. This gave 21 mg of the yellow title compound of m.p. 49-54° C.

Example 4

Preparation of N-acetyl-4-chloro-6-((S)-2,2,2-trifluoro-1-methylethylamino)-5-(2,4,6-trifluorophenyl)-pyrimidine-2-carboximide [I-12]

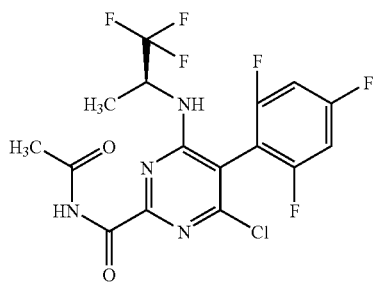

With ice bath cooling, 150 mg of amide (Example 1) in 10 ml of THF were reacted with 20 mg of sodium hydride, and the mixture was stirred for 30 min. 35 mg of acetyl chloride, dissolved in 1 ml of THF, were added slowly. The reaction mixture was stirred at room temperature for 30 min. Ice-water was then added to the reaction mixture, and the mixture was extracted with dichloromethane. The combined organic phases were dried over Mg₂SO₄ and concentrated using a rotary evaporator. This gave 65 mg of the red-brown title compound of m.p. 58-65° C.

Example 5

Preparation of isopropyl 4-chloro-6-((S)-2,2,2-trifluoro-1-methylethylamino)-5-(2,4,6-trifluorophenyl)pyrimidine-2-carboxylate [V-3]

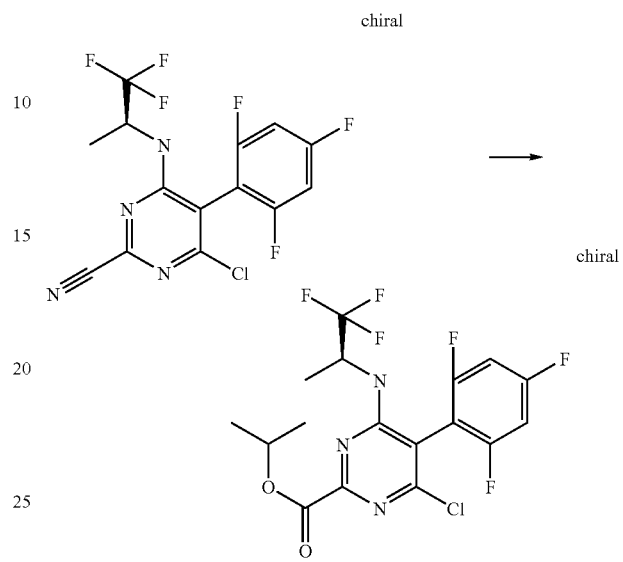

At room temperature, 22 g of 4-chloro-6-((S)-2,2,2-trifluoro-1-methylethylamino)-5-(2,4,6-trifluorophenyl)pyrimidine-2-carbonitrile were dissolved in 210 ml of isopropanol. Over a period of 30 min, HCl gas was introduced into the solution, and the mixture was then stirred at reflux for 96 h. The mixture was concentrated, water was added, followed by a top-layer of ethyl acetate, and the mixture was made alkaline using sodium carbonate. The ethyl acetate phase was dried with magnesium sulfate and concentrated using a rotary evaporator. This gave 21.4 g of a colorless solid.

Yield: 83.8%. m.p.: 146-147° C.

With appropriate modification of the starting materials, the procedures given in the synthesis examples above were used to obtain further compounds I. The compounds obtained in this manner are listed in the table 1 below, together with physical data.

TABLE IA

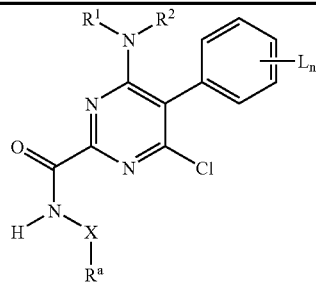

1A

| No. | RᵃX | R¹ | R² | Lₙ | m.p. [° C.] | ¹H-NMR [CDCl₃, ppm] |
|---|---|---|---|---|---|---|
| I-1 | H | (R,S)-CH(CH₃)CH(CH₃)₂ | H | 2,4,6-trifluoro | | 0.80-0.90 (m, 2CH₃), 1.15 (d, CH5), 1.75-1.85 (m, CH), 4.25-4.30 (m, CH), 4.60 (s, NH), 6.75 (s, NH), 6.80-6.90 (m, 2CH), 7.70 (s, NH) |

TABLE IA-continued

1A

| No. | R$^a$X | R$^1$ | R$^2$ | L$_n$ | m.p. [° C.] | $^1$H-NMR [CDCl$_3$, ppm] |
|---|---|---|---|---|---|---|
| I-2 | H | —(CH$_2$)$_2$CH(CH$_3$)(CH$_2$)$_2$— | | 2,4,6-trifluoro | 116-128 | |
| I-3 | H | —CH(CH$_3$)$_2$ | H | 2-chloro-6-fluoro | 208-210 | |
| I-4 | NH$_2$ | —CH(CH$_3$)$_2$ | H | 2-chloro-6-fluoro | 103-108 | |
| I-5 | H | (S)—CH(CH$_3$)CF$_3$ | H | 2,4,6-trifluoro | 157-162 | |
| I-6 | NH$_2$ | (S)—CH(CH$_3$)CF$_3$ | H | 2,4,6-trifluoro | 59-65 | |
| I-7 | H | —CH$_2$C=CH$_2$ | CH$_2$C=CH$_2$ | 2,4,6-trifluoro | 134-141 | |
| I-8 | CH$_3$ | —CH$_2$C=CH$_2$ | CH$_2$C=CH$_2$ | 2,4,6-trifluoro | 52-58 | |
| I-9 | —N(CH$_3$)$_2$ | (S)—CH(CH$_3$)CF$_3$ | H | 2,4,6-trifluoro | 39-45 | |
| I-10 | —C(CH$_3$)$_3$ | (S)—CH(CH$_3$)CF$_3$ | H | 2,4,6-trifluoro | 49-54 | |
| I-11 | —OH | (S)—CH(CH$_3$)CF$_3$ | H | 2,4,6-trifluoro | | 1.4 (d, CH3), 4.85 (d, NH), 5.60-5.80 (m, CH), 6.90-7.00 (m, CH), 10.5 (s(broad), OH) |
| I-12 | (C=O)CH$_3$ | (S)—CH(CH$_3$)CF$_3$ | H | 2,4,6-trifluoro | 58-65 | |
| I-13 | H | —CH(CH$_3$)CF$_3$ | H | 2,4,6-trifluoro | 222-224 | |
| I-14 | —CH$_3$ | (S)—CH(CH$_3$)CF$_3$ | H | 2,4,6-trifluoro | | 1.25 (d, 3H), 2.9 (d, 3H), 5.25 (m, 2H), 6.75 (m, 2H), 7.8 (s, 1H) |
| I-15 | H | —CH$_2$—COOH | H | 2,4,6-trifluoro | 227-228 | |
| I-16 | H | (R)—CH(CH$_3$)CH(CH$_3$)$_2$ | H | 2,4,6-trifluoro | | 0.75 (m, 6H), 1.1 (m, 3H), 1.75 (m, 1H), 4.2 (m, 1H), 4.4 (m, 1H), 5.8 (s, 1H), 7.25 (m, 2H), 7.4 (m, 1H), 7.6 (s, 1H) |
| I-17 | H | —CH(CH$_3$)$_2$ | H | 2-chloro-4-fluoro | 141-150 | |
| I-18 | H | —CH$_2$—C$_6$H$_5$ | H | 2-chloro-4-fluoro | 48-56 | |
| I-19 | H | (R)—CH(CH$_3$)CH(CH$_3$)$_2$ | H | 2,4-difluoro | | 0.75 (m, 6H), 1.1 (m, 3H), 1.75 (m, 1H), 4.2 (m, 1H), 4.5 (m, 1H), 5.85 (s, 1H), 7.1 (m, 2H), 7.3 (m, 1H), 7.6 (s, 1H) |
| I-20 | H | —CH$_2$—C$_6$H$_5$ | H | 2,4-difluoro | 53-58 | |
| I-21 | H | —CH(CH$_3$)$_2$ | H | 2,4-difluoro | 172-176 | |
| I-22 | H | —(CH$_2$)$_2$CH(CH$_3$)(CH$_2$)$_2$— | | 2,4-difluoro | 50-63 | |
| I-23 | H | (S)—CH(CH$_3$)CH(CH$_3$)$_2$ | H | 2,4-difluoro | 99-105 | |
| I-24 | H | (S)—CH(CH$_3$)CH(CH$_3$)$_2$ | H | 2-chloro-4-fluoro | 79-88 | |
| I-25 | H | —(CH$_2$)$_2$CH(CH$_3$)(CH$_2$)$_2$— | | 2,6-difluoro | 173-175 | |

TABLE IA-continued

1A

| No. | RªX | R¹ | R² | Lₙ | m.p. [° C.] | ¹H-NMR [CDCl₃, ppm] |
|---|---|---|---|---|---|---|
| I-26 | H | —(CH₂)₂CH(CH₃)(CH₂)₂— | | 2-chloro-4-fluoro | 175-177 | |
| I-27 | H | (S)—CH(CH₃)CF₃ | H | 2,6-difluoro | 206-208 | |
| I-28 | H | (S)—CH(CH₃)CH(CH₃)₂ | H | 2,6-difluoro | 128-130 | |
| I-29 | H | (S)—CH(CH₃)CF₃ | H | 2-chloro-4-fluoro | 165-167 | |
| I-30 | (C=O)CH₃ | —(CH₂)₂CH(CH₃)(CH₂)₂— | | 2-chloro-4-fluoro | | 0.9 (d, 3H), 1.0 (m, 2H), 2.6 (s, 3H), 4.0 (m, 2H), 7.1 (m, 1H), 7.25 (m, 2H), 10.0 (s, 1H) |
| I-31 | H | (S)—CH(CH₃)CH(CH₃)₂ | H | 2-chloro-4-methoxy | 84-88 | |
| I-32 | H | (S)—CH(CH₃)CF₃ | H | 2,4,6-trifluoro | | 1.4 (m, 3H), 3.9 (s, 3H), 5.0 (d, 1H), 5.25 (m, 1H), 6.8 (m, 2H) |
| I-33 | (C=O)CH₃ | —(CH₂)₂CH(CH₃)(CH₂)₂— | | 2,6-difluoro | | 0.9 (d, 3H), 1.0 (m, 2H), 1.6 (s, 3H), 2.8 (s, 3H), 4.0 (m, 2H), 7.0 (m, 2H), 7.45 (m, 1H), 10.0 (s, 1H) |

TABLE VA

VA

| No. | R' | R¹ | R² | Lₙ | m.p. [° C.] | ¹H-NMR [CDCl₃, ppm] |
|---|---|---|---|---|---|---|
| V-1 | CH₃ | (S)—CH(CH₃)CF₃ | H | 2,4,6-trifluoro | | 1.3 (d, 3H), 4.0 (s, 3H), 4.6 (d, NH), 5.25 (m, 1H), 6.9 (m, 2H) |
| V-2 | —CH(CH₃)₂ | —CH₂C=CH₂ | —CH₂C=CH₂ | 2,4,6-trifluoro | 53-57 | |
| V-3 | —CH(CH₃)₂ | (S)—CH(CH₃)CF₃ | H | 2,4,6-trifluoro | 146-147 | |
| V-4 | —CH₂CH₃ | (3)—CH(CH₃)CF₃ | H | 2,4,6-trifluoro | | 1.35 (d, 3H), 1.45 (t, 3H), 4.5 (q, 2H), 4.6 (d, NH), 5.3 (m, CH), 6.9 (m, 2H) |
| V-5 | —(CH₂)₂CH₃ | (3)—CH(CH₃)CF₃ | H | 2,4,6-trifluoro | 100-105 | |
| V-6 | —CH(CH₃)₂ | —CH₂CF₃ | H | 2,4,6-trifluoro | 115-118 | |
| V-7 | —(CH₂)₃CH₃ | (S)—CH(CH₃)CF₃ | H | 2,4,6-trifluoro | 71-75 | |

TABLE VA-continued

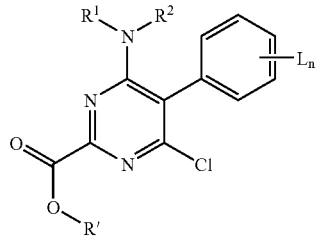

VA

| No. | RªX | R¹ | R² | $L_n$ | m.p. [° C.] | ¹H-NMR [CDCl₃, ppm] |
|---|---|---|---|---|---|---|
| V-8 | —(CH₂)₄CH₃ | (3) —CH(CH₃)CF₃ | H | 2,4,6-trifluoro | 82-88 | |
| V-9 | —(CH₂)₅CH₃ | (S)—CH(CH₃)CF₃ | H | 2,4,6-trifluoro | 57-60 | |
| V-10 | —CH₂CF₃ | (S)—CH(CH₃)CF₃ | H | 2,4,6-trifluoro | | 1.35 (d, 3H), 4.7 (d, NH), 4.8 (m, 2H), 5.3 (m, 1H), 6.9 (m, 2H) |
| V-11 | —(CH₂)₂CH(CH₃)₂ | (S)—CH(CH₃)CF₃ | H | 2,4,6-trifluoro | 90-93 | |
| V-12 | —CH₂CH(CH₃)—CH₂CH₃ | (S)—CH(CH₃)CF₃ | H | 2,4,6-trifluoro | 75-81 | |
| V-13 | —CH(CH₃)—(CH₂)₂CH₃ | (S)—CH(CH₃)CF₃ | | 2,4,6-trifluoro | | 0.9 (t, 3H), 1.3-1.9 (m, 13H), 4.55 (d, NH), 5.25 (m, 2H), 6.9 (m, 2H) |
| V-14 | —CH(CH₃)₂ | —(CH₂)₂CH(CH₃)(CH₂)₂— | | 2,4,6-trifluoro | | 0.8 (d, 3H), 0.9 (m, 2H), 1.4 (d, 6H), 1.5 (m, 3H), 2.7 (t, 2H), 3.9 (d, 2H), 5.2 (m, CH), 6.7 (m, 2H) |
| V-15 | —CH(CH₃)—CH(CH₃)₂ | (S)—CH(CH₃)CF₃ | H | 2,4,6-trifluoro | | 1.0 (m, 6H), 1.4 (m 6H), 2.0 (m, CH), 4.6 (m, NH), 5.0 (m, CH), 5.3 (m, CH), 6.9 (m, 2H) |
| V-16 | —CH₂C═CH₂ | (S)—CH(CH₃)CF₃ | H | 2,4,6-trifluoro | | 1.35 (d, 3H), 4.8 (d, 2H), 4.95 (d, 1H), 6.3 (m, 2H), 5.45 (d, 1H), 6.1 (m, 1H), 6.9 (m, 1H) |
| V-17 | —(CH₂)₂NH₂ | (S)—CH(CH₃)CF₃ | H | 2,4,6-trifluoro | | 1.0 (m, 6H), 1.4 (m 6H), 2.0 (m, CH), 4.6 (m, NH), 5.0 (m, CH), 5.3 (m, CH), 6.9 (m, 2H) |
| V-18 | cyclohexyl | (S)—CH(CH₃)CF₃ | H | 2,4,6-trifluoro | | 1.35 (d, 3H), 4.8 (d, 2H), 4.95 (d, 1H), 6.3 (m, 2H), 5.45 (d, 1H), 6.1 (m, 1H), 6.9 (m, 1H) |
| V-19 | —CH₂CH(CH₃)₂ | (S)—CH(CH₃)CF₃ | H | 2,4,6-trifluoro | 97-102 | |
| V-20 | —CH(CH₃)CH₂CH₃ | (S)—CH(CH₃)CF₃— | H | 2,4,6-trifluoro | 145-146 | |
| V-21 | —CH₂C₆H₅ | (S)—CH(CH₃)CF₃ | H | 2,4,6-trifluoro | | 1.4 (d, 3H), 4.55 (m, 3H), 5.25 (m, 1H), 6.9 (m, 2H), 7.3-7.5 (m, 5H) |
| V-22 | cyclopentyl | (S)—CH(CH₃)CF₃ | H | 2,4,6-trifluoro | 114-115 | |
| V-23 | cyclobutyl | (S)—CH(CH₃)CF₃ | H | 2,4,6-trifluoro | 127-129 | |

Examples of the action against harmful fungi

The fungicidal action of the compounds of the formula I was demonstrated by the following experiments:

The active compounds were prepared separately as a stock solution with 0.25% by weight of active compound in acetone or DMSO. 1% by weight of the emulsifier Uniperol® EL (wetting agent having emulsifying and dispersing action based on ethoxylated alkylphenols) was added to this solution. The stock solutions of the active compounds were diluted with water to the stated concentration.

USE EXAMPLES

1. Activity Against Late Blight on Tomatoes Caused by *Phytophthora infestans*, Protective Treatment Leaves of potted plants of the cultivar "Goldene Prinzessin" were sprayed to runoff point with an aqueous suspension having the concentration of active compound stated below. The next day, the leaves were infected with an aqueous sporangiophore suspension of *Phytophthora infestans*. The plants were then placed in a water-vaporsaturated chamber at 18-20° C. After 6 days, the late blight on the untreated, but infected control plants had developed to such an extent that the infection could be determined visually in %.

| No. | R⁴ | document | infection at 250 ppm of a.i. (% leaf area) |
|---|---|---|---|
| I-5 | —(C═O)NH₂ | according to the invention | 0 |
| V-3 | —(C═O)—O—CH(CH₃)₃ | according to the invention | 5 |
| V1 | —(C═NOCH₃)NH₂ | WO 03/043993 | 80 |
| | | untreated | 80 |

2. Persistency Against Early Blight on Tomatoes Caused by *Alternaria solani*, Protective Treatment Leaves of potted plants of the cultivar "Goldene Prinzessin" were sprayed to runoff point with an aqueous suspension having the concentration of active compound stated below.

To test for persistency, the leaves were infected with an aqueous spore suspension of *Alternaria solani* in a 2% strength biomalt solution having a density of $0.17 \times 10^6$ spores/ml only after seven days. The plants were then placed in a water-vapor-saturated chamber at 20-22° C. After a further 5 days, the disease on the untreated, but infected control plants had developed to such an extent that the infection could be determined visually in %.

| No. | R⁴ | document | infection at 16 ppm of a.i. (% leaf area) |
|---|---|---|---|
| I-5 | (C═O)NH₂ | according to the invention | 30 |
| V1 | (C═NOCH₃)NH₂ | WO 03/043993 | 67 |
| | | untreated | 90 |

3. Activity Against Gray Mold on Bell Pepper Leaves caused by *Botrytis cinerea*, Protective Application Bell pepper seedlings of the cultivar "Neusiedler Ideal Elite" were, after 2-3 leaves were well developed, sprayed to runoff point with an aqueous suspension having the concentration of active compound stated below. The next day, the treated plants were inoculated with a spore suspension of *Botrytis cinerea* which contained $1.7 \times 10^6$ spores/ml in a 2% strength aqueous biomalt solution, The test plants were then placed in a climatized chamber at 22-24° C., in the dark and at high atmospheric humidity. After 5 days, the extent of the fungal infection on the leaves could be determined visually in %.

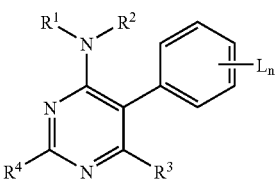

| No. | R⁴ | document | infection at 16 ppm of a.i. (% leaf area) |
|---|---|---|---|
| I-2 | —(C═O)NH₂ | according to the invention | 15 |
| V2 | —(C═NOCH₃)NH₂ | Example I-186 from WO 03/043993 | 90 |
| | | untreated | 100 |

We claim:
1. A 2-substituted pyrimidine of the formula I in which the index and the substituents are as defined below:

n is an integer from 1 to 5;

L is halogen, cyano, cyanato (OCN), $C_1$-$C_8$-alkyl, $C_2$-$C_8$-alkenyl, $C_2$-$C_8$-alkynyl, $C_1$-$C_6$-alkoxy, $C_2$-$C_8$-alkenyloxy, $C_2$-$C_8$-alkynyloxy, $C_3$-$C_6$-cycloalkyl, $C_4$-$C_6$-cycloalkenyl, $C_3$-$C_6$-cycoalkyloxy, $C_4$-$C_6$-cycloalkenyloxy, nitro, —C(═O)-A, —C(═O)—O-A, —C(═O)—N(A')A, C(A')(═N—OA), N(A')A, N(A')-C(═O)-A, N(A")-C(═O)—N(A')A, S(═O)$_m$-A, S(═O)$_m$—O-A or S(═O)$_m$—N(A')A, m is 0, 1 or 2;

A, A', A" independently of one another are hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, where the organic radicals may be partially or fully halogenated or may be substituted by nitro, cyanato, cyano or $C_1$-$C_4$-alkoxy; or A and A' together with the atoms to which they are attached are a five- or six-membered saturated, partially unsaturated or aromatic heterocycle which contains one to four heteroatoms from the group consisting of O, N and S;

where the aliphatic groups of the radical definitions of L for their part may be partially or fully halogenated or may carry one to four groups R";

R" is cyano, $C_1$-$C_6$-alkoxy, $C_3$-$C_6$-cycloalkyl, $C_2$-$C_8$-alkenyloxy, $C_2$-$C_8$-alkynyloxy, $C_4$-$C_6$-cycloalkenyl, $C_3$-$C_6$-cycloalkyloxy, $C_4$-$C_6$-cycloalkenyloxy, —C(=O)-A, —C(=O)—O-A, —C(=O)—N(A')A, C(A')(=N—OA), N(A')A, N(A')-C(=O)-A, N(A")-C(=O)—N(A')A, S(=O)$_m$-A, S(=O)$_m$—O-A or S(=O)$_m$—N(A')A;

$R^1$,$R^2$ independently of one another are $C_1$-$C_6$-alkyl, $C_2$-$C_6$-alkenyl, $C_2$-$C_6$-alkynyl, $C_3$-$C_6$-cycloalkyl, or $C_3$-$C_6$-halocycloalkyl, where the aliphatic group of the radical definitions of $R^1$ and $R^2$ for their part may be partially or fully halogenated or may carry one to four groups $R^v$:

$R^v$ is cyano, $C_3$-$C_6$-cycloalkyl, $C_4$-$C_6$-cycloalkenyl, hydroxyl, $C_1$-$C_6$-alkoxy, $C_2$-$C_8$-alkenyloxy, $C_2$-$C_8$-alkynyloxy, $C_3$-$C_6$-cycloalkyloxy, $C_4$-$C_6$-cycloalkenyloxy, $C_1$-$C_6$-alkylthio, —C(=O)-A, —C(=O)—O-A, —C(=O)—N(A')A, C(A')(=N—OA), N(A')A, N(A')-C(=O)-A, N(A")-C(=O)—N(A')A, S(=O)$_m$-A, S(=O)$_m$—O-A or S(=O)$_m$—N(A')A or phenyl, where the phenyl moiety may carry one to three radicals selected from the group consisting of: halogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_1$-$C_6$-alkoxy, cyano, nitro, —C(=O)-A, —C(=O)—O-A, —C(=O)—N(A')A, C(A')(-N—OA), N(A')A; or $R^2$ may additionally be hydrogen; or $R^1$ and $R^2$ may also, together with the nitrogen atom to which they are attached, form a saturated or unsaturated five- or six-membered ring which may be interrupted by an ether (—O—), carbonyl (C=O), thio (—S—), sulfoxyl (—S[=O]—) or sulfenyl (—SO$_2$—) or a further amino (—N($R^a$) group, where $R^a$ is hydrogen or $C_1$-$C_6$-alkyl, and/or may contain one or more substituents from the group consisting of halogen, $C_1$-$C_6$-alkyl, $C_1$-$C_6$-haloalkyl and oxy-$C_1$-$C_3$-alkyleneoxy;

$R^3$ is halogen, cyano, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy, $C_3$-$C_4$-alkenyloxy, $C_3$-$C_4$-alkynyloxy, $C_1$-$C_6$-alkylthio, di-($C_1$-$C_6$-alkyl)amino or $C_1$-$C_6$-alkylamino, where the alkyl, alkenyl and alkynyl radicals of $R^3$ may be substituted by halogen, cyano, nitro, $C_1$-$C_2$-alkoxy or $C_1$-$C_4$-alkoxycarbonyl;

$R^4$ corresponds to one of the formulae

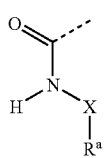 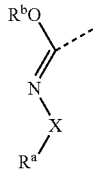

where

X is a direct bond, —(C=O)—, —(C=O)—NH—, —(C=O)—O—, —O—, —NR$^c$—, —CH$_2$O—(C=O)—, —CH=CH—(C=O)—, where in each case the left moiety is attached to the nitrogen atom;

$R^a$ is hydrogen, $C_1$-$C_6$-alkyl, $C_2$-$C_8$-alkenyl, $C_2$-$C_8$-alkynyl or benzyl;

$R^b$ is hydrogen, $C_1$-$C_6$-alkyl, $C_2$-$C_6$-alkenyl or $C_2$-$C_8$-alkynyl;

$R^c$ is hydrogen, $C_1$-$C_6$-alkyl, $C_2$-$C_6$-alkenyl, $C_2$-$C_8$-alkynyl, benzyl or $C_1$-$C_6$-acyl, where the aliphatic, alicyclic or aromatic groups of the radical definitions of $R^a$, $R^b$ and/or $R^c$ for their part may carry one to four groups $R^w$:

$R^w$ is halogen, cyano, OR$^x$, NHR$^x$, SR$^x$, $C_1$-$C_6$-alkyl, $C_2$-$C_6$-alkenyl, $C_2$-$C_6$-alkynyl, $C_1$-$C_6$-alkoxy, $C_1$-$C_4$-alkoxycarbonyl, $C_1$-$C_4$-acylamino, [1,3]dioxolane-$C_1$-$C_4$-alkyl, [1,3]dioxane-$C_1$-$C_4$-alkyl, where $R^x$ is hydrogen, $C_1$-$C_6$-alkyl, $C_2$-$C_8$-alkenyl, $C_2$-$C_8$-alkynyl or benzyl.

2. The 2-substituted pyrimidine of the formula I as claimed in claim 1 in which the index and the substituents are as defined below:

n is an integer from 1 to 3, where at least one substituent L is located in the ortho-position on the phenyl ring;

L is halogen, cyano, methyl, methoxy, —C(=O)—O-A, —C(=O)—N(A')A, C(A')(=N—OA), N(A')A, N(A')-C(=O)-A, A,A' independently of one another are hydrogen, $C_1$-$C_6$-alkyl, $C_2$-$C_6$-alkenyl, $C_2$-$C_6$-alkynyl, phenyl, where the organic radicals may be partially or fully halogenated or may be substituted by $C_1$-$C_4$-alkoxy; or A and A' together with the atoms to which they are attached are a five- or six-membered saturated heterocycle which contains one or two heteroatoms from the group consisting of O, N and S;

where the aliphatic groups of the radical definitions of L for their part may be partially or fully halogenated;

$R^1$,$R^2$ independently of one another are $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl or $C_2$-$C_6$-haloalkynyl;

$R^2$ may additionally be hydrogen;

$R^1$ and $R^2$ may also, together with the nitrogen atom to which they are attached, form a saturated or unsaturated five- or six-membered ring which may be interrupted by an ether (—O—) or a further amino (—N($R^a$) group, where $R^a$ is hydrogen or $C_1$-$C_6$-alkyl, and/or may contain one or more substituents from the group consisting of halogen, $C_1$-$C_6$-alkyl, $C_1$-$C_6$-haloalkyl and oxy-$C_1$-$C_3$-alkyleneoxy;

$R^3$ is halogen, cyano, $C_1$-$C_4$-alkyl, $C_1$-$C_4$-alkoxy or $C_1$-$C_4$-haloalkyl;

$R^4$ corresponds to one of the formulae

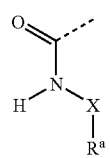 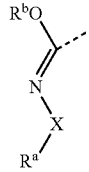

where

X is a direct bond, —(C=O)—, —(C=O)—NH—, —(C=O)—O—, —O—, —NR$^c$—, where in each case the left moiety is attached to the nitrogen atom;

$R^a$ is hydrogen, methyl, allyl or propargyl;

$R^b$ is hydrogen, $C_1$-$C_4$-alkyl, allyl or propargyl;

$R^c$ is hydrogen, methyl or $C_1$-$C_4$-acyl, where the aliphatic groups of the radical definitions of $R^a$, $R^b$ and/or $R^c$ for their part may carry one or two groups $R^w$:

$R^w$ is halogen, $OR^x$, $NHR^x$, $C_1$-$C_6$-alkyl, $C_1$-$C_4$-alkoxy-carbonyl, $C_1$-$C_4$-acylamino, [1,3]dioxolane-$C_1$-$C_4$-alkyl, [1,3]dioxane-$C_1$-$C_4$-alkyl, where $R^x$ is hydrogen, methyl, allyl or propargyl.

3. The 2-substituted pyrimidine as claimed in claim 1 in which $R^3$ is chlorine, cyano, methyl or methoxy.

4. The 2-substituted pyrimidine as claimed in claim 1 in which $R^4$ corresponds to a formula

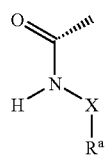

where X is a direct bond, —O— or —(C=O)—O—, and $R^a$ is hydrogen or $C_1$-$C_6$-alkyl.

5. The 2-substituted pyrimidine as claimed in claim 1 in which the phenyl group substituted by $L_n$ is the group B

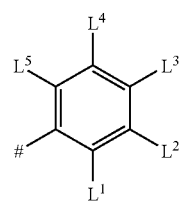

where # is the point of attachment to the pyrimidine skeleton and $L^1$ is fluorine, chlorine, $CH_3$ or $CF_3$;

$L^2$, $L^4$ independently of one another are hydrogen, $CH_3$ or fluorine;

$L^3$ is hydrogen, fluorine, chlorine, cyano, $CH_3$, $SCH_3$, $OCH_3$, $SO_2CH_3$, NH—C(=O)$CH_3$, N($CH_3$)—C(=O)$CH_3$ or $COOCH_3$ and $L^5$ is hydrogen, fluorine, chlorine or $CH_3$.

6. A process for preparing the compounds IA by hydrolysis of the nitriles of the formula IV, where the substituents $R^1$, $R^2$, $R^3$ and L and the index n are as defined in claim 1, which comprises carrying out the hydrolysis in the presence of a base and hydrogen peroxide.

7. A process for preparing the compounds IA' and IC according to the invention where the substituents $L_n$, $R^1$, $R^2$, $R^3$, X, $R^a$ and $R^b$ are as defined in claim 1, which process uses nitriles of the formula IV -continued

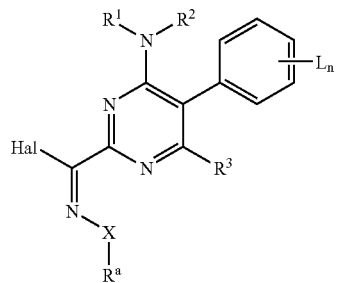

VI

1. R$^b$—OH
2. base →

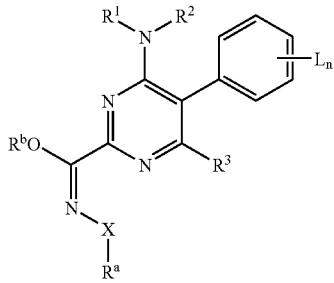

IC which are converted with alcohols of the formula R'OH, where R' is $C_1$-$C_8$-alkyl, $C_2$-$C_8$-alkenyl, $C_2$-$C_8$-alkynyl or $C_3$-$C_6$-cycloalkyl, where the radicals alkyl, alkenyl and alkynyl may be partially or fully halogenated and may carry one to three groups R$^v$, into the esters of the formula V, which are then, using amines R$^a$—X—NH$_2$ and added dehydrating agents, converted into the amides IA' and thither, in the presence of carbon tetrahalide and triarylphosphine, into the imine halides of the formula VI and finally, with alcohols of the formula R$^b$OH and bases, into the imino ethers of the formula IC.

8. An ester of the formula V

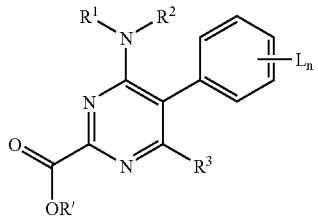

V in which the substituents are as defined below:

n is an integer from 1 to 5;

L is halogen, cyano, cyanato (OCN), $C_1$-$C_8$-alkyl, $C_2$-$C_8$-alkenyl, $C_2$-$C_8$-alkynyl, $C_1$-$C_6$-alkoxy, $C_2$-$C_8$-alkenyloxy, $C_2$-$C_8$-alkynyloxy, $C_3$-$C_6$-cycloalkyl, $C_4$-$C_6$-cycloalkenyl, $C_3$-$C_6$-cycoalkyloxy, $C_4$-$C_6$-cycloalkenyloxy, nitro, —C(=O)-A, —C(=O)—O-A, —C(=O)—N(A')A, C(A')(=N—OA), N(A')A, N(A')-C(=O)-A, N(A")-C(=O)—N(A')A, S(=O)$_m$-A, S(=O)$_m$—O-A or S(=O)$_m$—N(A')A, m is 0, 1 or 2;

A, A', A" independently of one another are hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, where the organic radicals may be partially or fully halogenated or may be substituted by nitro cyanato cyano or $C_1$-$C_4$-alkoxy; or A and A' together with the atoms to which the are attached form a five- or six-membered saturated, partially unsaturated or aromatic heterocycle which contains one to four heteroatoms from the group consisting of O, N and S;

where the aliphatic groups of the radical definitions of L for their part may be partially or fully halogenated or may carry one to four groups R$^u$;

R$^2$ is cyano, $C_1$-$C_6$-alkoxy, $C_3$-$C_6$-cycloalkyl, $C_2$-$C_8$-alkenyloxy, $C_2$-$C_8$-alkynyloxy, $C_4$-$C_6$-cycloalkenyl, $C_3$-$C_6$-cycloalkyloxy, $C_4$-$C_6$-cycloalkenyloxy, —C(=O)-A, —C(=O)—O-A, —C(=O)—N(A') A, C(A')(=N—OA), N(A')A, N(A')-C(=O)-A, N(A")-C(=O)—N(A')A, S(=O)$_m$-A, S(=O)$_m$—O-A or S(=O)$_m$—N(A')A;

R$^1$,R$^2$ independently of one another are $C_1$-$C_6$-alkyl, $C_2$-$C_6$-alkenyl, $C_2$-$C_6$-alkynyl, $C_3$-$C_6$-cycloalkyl, or $C_3$-$C_6$-halocycloalkyl, where the aliphatic group of the radical definitions of R$^1$ and R$^2$ for their part may be partially or fully halogenated or may carry one to four groups R$^v$:

R$^v$ is cyano, $C_3$-$C_6$-cycloalkyl, $C_4$-$C_6$-cycloalkenyl, hydroxyl, $C_1$-$C_6$-alkoxy, $C_2$-$C_8$-alkenyloxy, $C_2$-$C_8$-alkynyloxy, $C_3$-$C_6$-cycloalkyloxy, $C_4$-$C_6$-cycloalkenyloxy, $C_1$-$C_6$-alkylthio, —C(=O)-A, —C(=O)—O-A, —C(=O)—N(A')A, C(A')(=N—OA), N(A')A, N(A')-C(=O)-A, N(A")-C(=O)—N (A')A, S(=O)$_m$-A, S(=O)$_m$—O-A or S(=O)$_m$—N (A")A or phenyl, where the phenyl moiety may carry one to three radicals selected from the group consisting of: halogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_1$-$C_6$-alkoxy, cyano, nitro, —C(=O)-A, —C(=O)—O-A, —C(=O)—N(A')A, C(A')(-N—OA), N(A')A; or R$^2$ additionally be hydrogen; or R$^1$ and R$^2$ may also, together with the nitrogen atom to which they are attached, form a saturated or unsaturated five- or six-membered ring which may be interrupted by an ether (—O—), carbonyl (C=O), thio (—S—), sulfoxyl (—S[=O]—) or sulfenyl (—SO$_2$—) or a further amino (—N(R$^a$) group, where R$^a$ is hydrogen or $C_1$-$C_6$-alkyl, and/or may contain one or more substituents from the group consisting of halogen, $C_1$-$C_6$-alkyl, $C_1$-$C_6$-haloalkyl and oxy-$C_1$-$C_3$-alkyleneoxy;

R$^3$ is halogen, cyano, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy, $C_3$-$C_4$-alkenyloxy, $C_3$-$C_4$-alkynyloxy, $C_1$-$C_6$-alkylthio, di-($C_1$-$C_6$-alkyl)amino or $C_1$-$C_6$-alkylamino, where the alkyl, alkenyl and alkynyl radicals of R$^3$ may be substituted by halogen, cyano, nitro, $C_1$-$C_2$-alkoxy or $C_1$-$C_4$-alkoxycarbonyl;

R' is $C_1$-$C_8$-alkyl, $C_2$-$C_8$-alkenyl, $C_2$-$C_8$-alkynyl or $C_3$-$C_6$-cycloalkyl, where the radicals alkyl, alkenyl and alkynyl may be partially or fully halogenated and may carry one to three groups $R^v$.

9. The ester as claimed in claim 8 where R' is isopropyl.

10. An imine halide of the formula VI

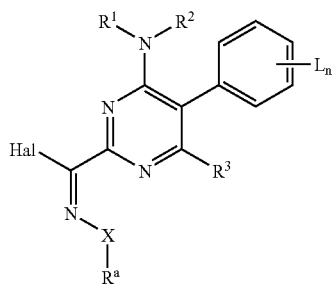

VI where the substituents are as defined below:

n is an integer from 1 to 5;

L is halogen, cyano, cyanato (OCN), $C_1$-$C_8$-alkyl, $C_2$-$C_8$-alkenyl, $C_2$-$C_8$-alkynyl, $C_1$-$C_6$-alkoxy, $C_2$-$C_8$-alkenyloxy, $C_2$-$C_8$-alkynyloxy, $C_3$-$C_6$-cycloalkyl, $C_4$-$C_6$-cycloalkenyl, $C_3$-$C_6$-cycoalkyloxy, $C_4$-$C_6$-cycloalkenyloxy, nitro, —C(=O)-A, —C(=O)—O-A, —C(=O)—N(A')A, C(A')(=N—OA), N(A')A, N(A')-C(=O)-A, N(A'')-C(=O)—N(A')A, S(=O)$_m$-A, S(=O)$_m$—O-A or S(=O)$_m$—N(A')A, m is 0, 1 or 2;

A, A', A'' independent of one another are hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, where the organic radicals may be partially or fully halogenated or may be substituted by nitro, cyanato, cyano or $C_1$-$C_4$-alkoxy; or A and A' together with the atoms to which they are attached are a five- or six-membered saturated, partially unsaturated or aromatic heterocycle which contains one to four heteroatoms from the group consisting of O, N and S;

where the aliphatic groups of the radical definitions of L for their part may be partially or fully halogenated or may carry one to four groups $R^u$;

$R^u$ is cyano, $C_1$-$C_6$-alkoxy $C_3$-$C_6$-cycloalkyl, $C_2$-$C_8$-alkenyloxy, $C_2$-$C_8$-alkynyloxy, $C_4$-$C_6$-cycloalkenyl, $C_3$-$C_6$-cycloalkyloxy, $C_4$-$C_6$-cycloalkenyloxy, —C(=O)-A, —C(=O)—O-A, —C(=O)—N(A')A, C(A')(=N—OA), N(A')A, N(A')-C(=O)-A, N(A'')-C(=O)—N(A')A, S(=O)$_m$A, S(=O)$_m$—O-A or S(=O)$_m$—N(A')A;

$R^1$,$R^2$ independently of one another are $C_1$-$C_6$-alkyl, $C_2$-$C_6$-alkenyl, $C_2$-$C_6$-alkynyl, $C_3$-$C_6$-cycloalkyl, or $C_3$-$C_6$-halocycloalkyl, where the aliphatic group of the radical definitions of $R^1$ and $R^2$ for their part may be partially or fully halogenated or may carry one to four groups $R^v$:

$R^v$ is cyano, $C_3$-$C_6$-cycloalkyl, $C_4$-$C_6$-cycloalkenyl, hydroxyl, $C_1$-$C_6$-alkoxy, $C_2$-$C_8$-alkenyloxy, $C_2$-$C_8$-alkynyloxy, $C_3$-$C_6$-cycloalkyloxy, $C_4$-$C_6$-cycloalkenyloxy, $C_1$-$C_6$-alkylthio, —C(=O)-A, —C(=O)—O-A, —C(=O)—N(A')A, C(A')(=N—OA'), N(A')A, N(A')-C(=O)-A, N(A'')-C(=O)—N(A')A, S(=O)$_m$-A, S(=O)$_m$—O-A or S(=O)$_m$—N(A')A or phenyl, where the phenyl moiety may carry one to three radicals selected from the group consisting of: halogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_1$-$C_6$-alkoxy, cyano, nitro, —C(=O)-A, —C(=O)—O-A, —C(=O)—N(A')A, C(A')(-N—OA), N(A')A; or $R^2$ may additionally be hydrogen; or $R^1$ and $R^2$ may also, together with the nitrogen atom to which they are attached, form a saturated or unsaturated five- or six-membered ring which may be interrupted by an ether (—O—), carbonyl (C=O), thio (—S—), sulfoxyl (—S[=O]—) or sulfenyl (—SO$_2$—) or a further amino (—N($R^a$) group, where $R^a$ is hydrogen or $C_{1-C6}$-alkyl, and/or may contain one or more substituents from the group consisting of halogen, $C_1$-$C_6$-alkyl, $C_1$-$C_6$-haloalkyl and oxy-$C_1$-$C_3$-alkyleneoxy;

$R^3$ is halogen, cyano, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy, $C_3$-$C_4$-alkenyloxy, $C_3$-$C_4$-alkynyloxy, $C_1$-$C_6$-alkylthio, di-($C_1$-$C_6$-alkyl)amino or $C_1$-$C_6$-alkylamino, where the alkyl, alkenyl and alkynyl radicals of $R^3$ may be substituted by halogen, cyano, nitro, $C_1$-$C_2$-alkoxy or $C_1$-$C_4$-alkoxycarbonyl;

X is a direct bond, —(C=O)—, —(C=O)—NH—, —(C=O)—O—, —O—, —NR$^c$—, —CH$_2$O—(C=O)—, —CH=CH—(C=O)—, where in each case the left moiety is attached to the nitrogen atom;

$R^a$ is hydrogen $C_1$-$C_6$-alkyl, $C_2$-$C_8$-alkenyl, $C_2$-$C_8$-alkynyl or benzyl; and Hal is fluorine, chlorine, bromine or iodine.

11. A pesticide which comprises a solid or liquid carrier and a compound of the formula I as claimed in claim 1.

12. A pesticide which comprises a solid or liquid carrier and a compound of the formula V as claimed in claim 8.

13. A method for controlling phytopathogenic harmful fungi, which comprises treating the fungi or the materials, plants, the soil or the seeds to be protected against fungal attack with an effective amount of a compound of the formula I as claimed in claim 1.

14. A method for controlling phytopathogenic harmful fungi, which comprises treating the fungi or the materials, plants, the soil or the seeds to be protected against fungal attack with an effective amount of a compound of the formula V as claimed claim 8.

* * * * *